US012691200B2

(12) United States Patent
Greenhalgh et al.

(10) Patent No.: US 12,691,200 B2
(45) Date of Patent: Jul. 28, 2026

(54) BONE GRAFT COMPOSITION

(71) Applicant: SURGENTEC, LLC, Boca Raton, FL (US)

(72) Inventors: Travis Greenhalgh, Boca Raton, FL (US); Andrew Shoup, Ft. Lauderdale, FL (US)

(73) Assignee: SurGen Tec, LLC, Boca Raton, FL (US)

( * ) Notice: Subject to any disclaimer, the term of this patent is extended or adjusted under 35 U.S.C. 154(b) by 945 days.

(21) Appl. No.: 17/759,093

(22) PCT Filed: Sep. 25, 2020

(86) PCT No.: PCT/US2020/052950
    § 371 (c)(1),
    (2) Date: Jul. 19, 2022

(87) PCT Pub. No.: WO2021/062324
    PCT Pub. Date: Apr. 1, 2021

(65) Prior Publication Data
    US 2023/0053789 A1      Feb. 23, 2023

Related U.S. Application Data

(60) Provisional application No. 62/906,088, filed on Sep. 25, 2019.

(51) Int. Cl.
    *A61L 27/12*      (2006.01)
    *A61L 27/10*      (2006.01)
    *A61L 27/18*      (2006.01)
    *A61L 27/20*      (2006.01)
    *A61L 27/36*      (2006.01)
    *A61L 27/58*      (2006.01)
    *C03B 19/06*      (2006.01)

(52) U.S. Cl.
    CPC .............. *A61L 27/12* (2013.01); *A61L 27/10* (2013.01); *A61L 27/18* (2013.01); *A61L 27/20* (2013.01); *A61L 27/3608* (2013.01); *A61L 27/58* (2013.01); *C03B 19/06* (2013.01); *A61L 2430/02* (2013.01); *A61L 2430/38* (2013.01)

(58) Field of Classification Search
    None
    See application file for complete search history.

(56) References Cited

U.S. PATENT DOCUMENTS

| | | | |
|---|---|---|---|
| 6,338,752 B1 | 1/2002 | Lin et al. | |
| 2004/0097612 A1* | 5/2004 | Rosenberg | .............. A61L 27/50 523/113 |
| 2005/0187140 A1* | 8/2005 | Hunter | .................... A61L 27/54 606/76 |
| 2011/0159057 A1 | 6/2011 | Da Silva Santos et al. | |
| 2013/0244942 A1* | 9/2013 | Benedict | ............. A61L 27/3608 514/16.7 |
| 2019/0167853 A1* | 6/2019 | Brunelle | ................. A61L 27/50 |
| 2019/0216983 A1 | 7/2019 | Segal et al. | |
| 2021/0008245 A1* | 1/2021 | Borden | ................... A61L 31/14 |

FOREIGN PATENT DOCUMENTS

WO      2010065780 A1      6/2010

OTHER PUBLICATIONS

Thongtrangan, I., et al., "Vertebral body replacement with an expandable cage for reconstruction after spinal tumor resection," Neurosurg Focus 15(5): Article 8 (2003). (Year: 2003).*
International Search Report and Written Opinion issued for PCT Application No. PCT/US2020/052950 dated Jan. 4, 2021.

* cited by examiner

*Primary Examiner* — David J Blanchard
*Assistant Examiner* — Daniel F Coughlin
(74) *Attorney, Agent, or Firm* — Knobbe, Martens, Olson & Bear, LLP

(57)      ABSTRACT

A particle comprising hydroxyapatite, β-tricalcium phosphate, α-tricalcium phosphate, and/or bioactive glass is provided. The particle can be useful in bone graft compositions further comprising a carrier. The composition can include a quadphasic particle having hydroxyapatite, β-tricalcium phosphate, α-tricalcium phosphate, bioactive glass, and a carrier. The particle can have a size in the range of 50 microns to 2.5 mm. A method of repairing a bone defect is also provided. The method can include a step of applying the bone graft composition to a subject having the bone defect, such as a spinal bone defect. The subject receiving the bone graft composition can be a mammal, namely a human, pet, or domestic animal.

39 Claims, 10 Drawing Sheets

Defect Left 4 Weeks Post-op
Empty (Negative Control)

Right 4 Weeks Post-op
EXAMPLE 1

Right 4 Weeks Post-op
EXAMPLE 2

Left 4 Weeks Post-op
COMPARATIVE EXAMPLE

Right 8 Weeks Post-op
Empty (Negative Control)

Right 8 Weeks Post-op
EXAMPLE 1

Left 8 Weeks Post-op
EXAMPLE 2

Right 8 Weeks Post-op
COMPARATIVE EXAMPLE

Right 12 Weeks Post-op
Empty (Negative Control)

Right 12 Weeks Post-op Test #1
EXAMPLE 1

Right 12 Weeks Post-op
COMPARATIVE EXAMPLE

Left 12 Weeks Post-op
EXAMPLE 2

BONE GRAFT COMPOSITION

RELATED APPLICATIONS AND INCORPORATION BY REFERENCE

This application is a U.S. national stage application under 35 U.S.C. § 371 of International Application No. PCT/US2020/052950, filed Sep. 25, 2020, which claims the benefit under 35 U.S.C. § 119(e) of U.S. Provisional Patent Application No. 62/906,088, filed Sep. 25, 2019, the entire disclosures of which are incorporated herein by reference.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This disclosure relates generally to bone graft compositions, kits comprising the same, methods of using the bone graph composition and methods of making the bone graft composition; and more particularly, to triphasic and quadphasic synthetic bone graft compositions comprising particles comprising hydroxyapatite, β-tricalcium phosphate, α-tricalcium phosphate, and/or bioactive glass, and a carrier. This disclosure also relates to methods for making and using the bone graft compositions.

BACKGROUND OF THE INVENTION

In bone grafting procedures, surgeons place bone or a bone substitute into a defect area of a patient's body to provide a scaffold for bone growth and repair. Bone grafts can be used to treat various orthopedic problems, for example, to fuse a joint or repair a fracture. Bone graft material can be, for example, autogenous (harvested from the patient's own body), allogeneic (harvested from another person, usually a cadaver), or synthetic. Autograft is generally preferred, but the autograft material must be extracted from the patient, which is adds an additional step to the procedure and is not always possible depending on the patient's condition and quality of bone. Allograft is a common substitute, but because it comes from a donor there is a risk of contamination or disease transmission. It also is difficult and expensive to process, distribute, and store allograft tissue. Further, demineralized bone matrix (DBM) and other allograft compositions can vary significantly from donor to donor, and generally do not require testing to prove efficacy. Such issues with autograft and allograft compositions make synthetic bone graft an attractive alternative. Synthetic materials provide scaffolding similar to bone and they can cause osteostimulation that attracts bone forming cells to the surgical site. Depending on the makeup of the composition, synthetic bone grafts can be easier to store and transport than allografts because of the temperature and regulatory restrictions for allografts.

During minimally invasive bone graft procedures, bone graft compositions are typically extruded through small elongated tubes. Such devices typically have a bore diameter size large enough to prevent the graft composition from clogging the tube due to the high viscosity of typical compositions. The process can require a substantial amount of force depending on the size and shape of the particles in the composition, as well as the viscosity of the composition. Under increased pressure, existing compositions tend to separate and lose homogeneity. Additionally, if the composition includes a mixture of different sized particles, the large and small sized particles may aggregate into different areas when pushed through a small cannula. The non-homogeneous mixture of particles may cause uneven resorption of the material and lead to poor bone growth. This effect may be compounded further if the composition comprises a plurality of different materials. Accordingly, a mixture of materials within a graft composition should be generally homogeneous to obtain the desired effects. Uncontrolled absorption and/or other negative effects may occur if the materials are not mixed into substantially homogeneous compositions. The loss of structural integrity can adversely affect the bone regeneration properties of the bone graft.

Bone graft composition can be pre-packaged in plastic shells or wide-bore syringes that are generally used in open surgeries or to fill an implant before it is placed into the body. Existing bone graft compositions lack the consistency needed for various delivery methods. For example, in open surgeries, it would be better to have a firmer and more moldable bone graft composition so it maintains its shape after the user places it into the target location. In minimally invasive surgery, on the other hand, it is important for the bone graft composition to be softer and more flowable so it can be dispensed through a small incision in route to the surgical site. Accordingly, different bone graft compositions are used for different packaging formats. A bone graft composition having a more flowable consistency and applicability to different packaging formats would provide an unexpected improvement.

Citation or identification of any document in this application is not an admission that such document is available as prior art to the present invention.

SUMMARY OF THE INVENTION

The present disclosure provides quadraphasic particles that are useful in bone graft compositions, the particles comprising hydroxyapatite, β-tricalcium phosphate, α-tricalcium phosphate, and/or bioactive glass. In some embodiments, the particles can be biphasic, triphasic, or quadphasic.

The quadphasic particles can comprise about 40 wt. % to about 60 wt. % hydroxyapatite, wherein the particle size of the hydroxyapatite ranges from about 2 μm to about 20 μm as determined by scanning electron microscopy and particle size analysis, about 30 wt. % to about 50 wt. % β-tricalcium phosphate wherein the particle size of the β-tricalcium phosphate ranges from about 2 μm to about 20 μm as determined by scanning electron microscopy and particle size analysis, about 5 wt. % to about 25 wt. % α-tricalcium phosphate, wherein the particle size of the α-tricalcium phosphate ranges from about 50 μm to about 100 μm as determined by scanning electron microscopy and particle size analysis, and about 5 wt. % to about 20 wt. % bioactive glass, wherein the particle size of the bioactive glass ranges from about 20 μm to about 90 μm as determined by scanning electron microscopy and particle size analysis. Particle size analysis involves use of a laser diffraction particle size analyzer wherein the sample is dispersed in a 50:50 mixture of glycerin:deionized ultra-filtered water to maintain suspension of the particles during analysis. The overall size of the triphasic particles ranges from about 50 μm to about 2.5 mm.

In some embodiments, the particles are biphasic, comprising 40 wt. % to about 60 wt. % hydroxyapatite wherein the presintering particle size of the hydroxyapatite ranges from about 2 μm to about 20 μm as determined by scanning electron microscopy and presintering particle size analysis and about 40 wt. % to about 60 wt. % β-tricalcium phosphate wherein the particle size of the β-tricalcium phosphate ranges from about 2 μm to about 20 μm as determined by scanning electron microscopy and particle size analysis. Particles are broken down and sieved one or more times to acquire the desired size. Particle size analysis involves use of a laser diffraction particle size analyzer wherein the sample is dispersed in a 50:50 mixture of glycerin:deionized ultra-filtered water to maintain suspension of the particles during analysis. The overall size of the biphasic particles ranges from about 50 μm to about 2.5 mm.

In some embodiments, the particles are triphasic, comprising about 40 wt. % to about 60 wt. % hydroxyapatite, wherein the particle size of the hydroxyapatite ranges from about 2 μm to about 40 μm as determined by scanning electron microscopy and particle size analysis, about 30 wt. % to about 50 wt. % β-tricalcium phosphate wherein the particle size of the β-tricalcium phosphate ranges from about 2 μm to about 40 μm as determined by scanning electron microscopy and particle size analysis, and about 5 wt. % to about 25 wt. % α-tricalcium phosphate, wherein the particle size of the α-tricalcium phosphate ranges from about 20 μm to about 100 μm as determined by scanning electron microscopy and particle size analysis. Particle size analysis involves use of a laser diffraction particle size analyzer wherein the sample is dispersed in a 50:50 mixture of glycerin:deionized ultra-filtered water to maintain suspension of the particles during analysis. The overall size of the triphasic particles ranges from about 50 μm to about 2.5 mm.

The present disclosure also provides methods for making the quadphasic particles biphasic, and triphasic particles that are useful in bone graft compositions. In some embodiments, the respective components of biphasic, triphasic, or quadphasic particles (see herein discussions of biphasic, triphasic, and quadphasic particles and components thereof) are sintered together at a temperature from about 500° C. to about 1700° C. to form the respective biphasic, triphasic, and quadphasic particle. In some embodiments, the respective components of biphasic, triphasic, or quadphasic particles can be mixed by hand or by machine to form a homogeneous mixture prior to sintering. The invention accordingly comprehends that the particle is a sintered particle.

The present disclosure also provides bone graft compositions wherein the bone graft compositions comprise at least the biphasic, triphasic, and/or quadphasic particle and a carrier. The carrier provides benefits to the composition such as assisting in the handling, flowability, cohesiveness, texturing, wicking, bonding, shaping, handling, packaging, stimulating bone growth, expanding, hardening of the composition. In some embodiments, the carrier may be a bioresorbable polymer. The carrier may comprise a single compound or a mixture of compounds and may comprise embedded hydroxyapatite and/or bioactive glass substrate.

In some embodiments, the bone graft composition comprises a biphasic particle and a carrier. The composition comprises about 30 wt. % to about 70 wt. % of the biphasic particles and about 30 wt. % to about 70 wt. % of the carrier.

In some embodiments, the bone graft composition comprises a triphasic particle and a carrier. The composition comprises about 30 wt. % to about 70 wt. % of the triphasic particles and about 30 wt. % to about 70 wt. % of the carrier.

In some embodiments, the bone graft composition comprises a quadphasic particle and a carrier. The composition comprises about 30 wt. % to about 70 wt. % of the quadphasic particles and about 30 wt. % to about 70 wt. % of the carrier. In a preferred embodiment, the composition comprises about 40 wt. % to about 55 wt. % of the quadphasic particles and about 45 wt. % to about 60 wt. % of the carrier.

The bone graft composition as described is useful in repairing a bone defect. The present invention comprehends uses of the biphasic, triphasic, and quadphasic particles in the manufacture of a medicament composition for repairing a bone defect in a mammal such as a human in need thereof. The present invention also contemplates the repair of a bone defect in pets and domestic animals such as canines, felines, porcines, equines, bovines, ovines, and caprinae. The present disclosure also provides a method of repairing a bone defect. In some embodiments, the method comprises a step of applying the bone graft composition described herein to a patient having the bone defect, such as a spinal bone defect.

A kit for bone graft procedures is also provided. In some embodiments, the kit includes the bone graft composition and a delivery device for administering the composition to a human patient, pet, or domestic animal.

In some embodiments the kit can also include an additional implantation device such as a 3D printed cage or loading case/retainer for implanting the bone graft composition. The bone graft composition can be injected into the cage or loading case/retainer to fill the implant. The cage or loading case/retainer can be configured to connect to a syringe or graft delivery system to facilitate transfer of the bone graft composition.

In some embodiments the kit can also include an implant that is intended to be filled with the bone graft composition. The bone graft composition may be injected into the implant with a filling device such as but not limited to, a ratcheting gun, piston syringe, funnel, threaded torque syringe or manual syringe. The kit can also include adapters that allow the bone graft composition to be filled into different sizes and shapes of implants.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
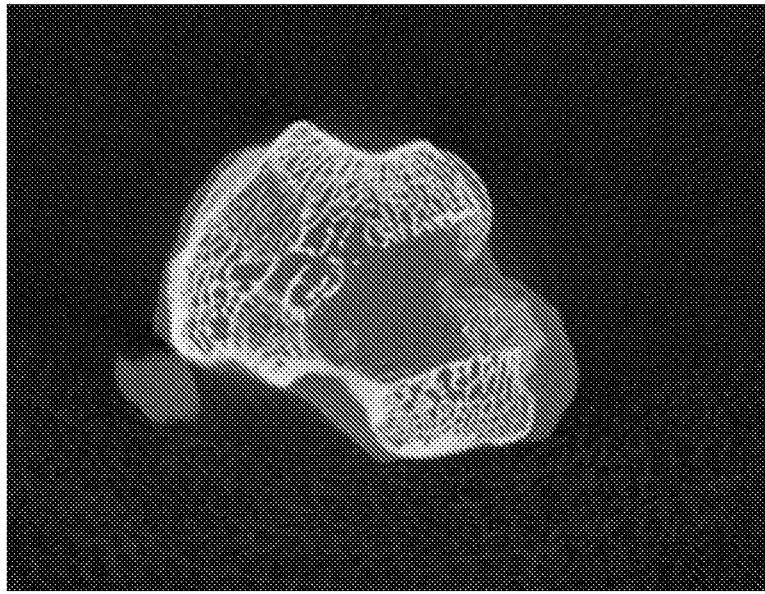
FIG. 1 is a Computed Tomography (CT scan) image of a rabbit hip with a drilled void remaining unfilled with bone graft (Negative Control), four (4) weeks after surgery.

Reference will now be made in detail to the present preferred embodiment(s), examples of which are illustrated in the accompanying drawings.

Unless defined otherwise, all technical and scientific terms used herein have the same meaning as commonly understood by those of ordinary skill in the art to which this application belongs. Although any methods and materials similar or equivalent to those described herein can be used in the practice or testing of embodiments of the present application, the preferred methods and materials are described. Generally, nomenclatures utilized in connection with, and techniques of chemistry are those known and commonly used in the art. Certain experimental techniques, not specifically defined, are generally performed according to conventional methods known in the art.

As used herein, the singular forms "a," "an," and "the" include the plural reference, and reference to a particular numerical value includes at least that particular value, unless the context clearly indicates otherwise. The terms "substantial," "substantially," and variations thereof are intended to note that a described feature is equal or approximately equal to a value or description. When values are expressed as approximations, by use of the antecedent "about," it will be understood that the particular value forms another embodiment. Where recited, all ranges are inclusive and combinable.

The terms "free" and "substantially free," when used to describe the concentration and/or absence of a particular component in a glass composition, means that the component was not intentionally added to the glass raw materials or composition. However, if present, the content of the component in the composition reaches only the level of an impurity unavoidably included in the process of preparing the composition.

As used herein, the term "biocompatible" refers to a property of a composition or material that relates to causing an appropriate host response in a specific application, or at least not causing a toxic or otherwise deleterious effect on a biological system of the host (locally or systemically).

As used herein, the term "osteoconductive" refers a property of a composition or material that relates to passively causing bone growth on a surface of the material and/or in an opening (e.g., a pore) of the material.

As used herein, the term "osteoinductive" refers to a property of a composition or material that relates to actively stimulating a biological response to induce bone formation. Osteoinduction can include the formation and/or stimulation of osteoprogenitor cells, including osteoprogenitor cells in bodily tissue surrounding or proximate to a graft or implant.

As used herein, the term "osteostimulation" refers to a property of a composition or material that relates to actively stimulating osteoblast proliferation and differentiation.

As used herein, the term "bioactive" refers to a property of a composition or material in which the material is capable of effecting a living organism, tissue, or cell.

As used herein, the term "biodegradable" refers to a property of a composition or material that relates to the degradation, disassembly, and/or digestion over time by action of a biological environment (including the action of living organisms, e.g., a patient's body), and/or in response to a change in physiological pH or temperature.

As used herein, the term "biphasic" refers to a material consisting of two different components combined into one particle.

As used herein, the term "triphasic" refers to a material consisting of three different components combined into one particle.

As used herein, the term "quadphasic" refers to a material consisting of four different components combined into one particle.

As used herein, the term "resorbable" refers to a property of a composition or material that relates to the capability of a material to be broken down over a period of time and assimilated into the biological environment.

As used herein, the phrase "non-load bearing application" refers to an application for repair of a void or gap in a bone or another bony structure in which the void or gap to be repaired is not intrinsic to the stability of the bone or bony structure.

As used herein, references to a weight of components of a particle described herein, such as the phrase "by weight" or "wt. %" refer to the mass fraction of the specified component of the particle relative to the total mass of the particle.

As used herein, references to a weight of components of a bone graft composition or material described herein, such as the phrase "by weight," or "wt. %," or "% w/w" refer to the mass fraction of the specified component of the bone graft composition or composition relative to the total mass of the bone graft composition or material. The total mass of the bone graft composition or composition includes the mass of the carrier component.

As used herein, references to a volume of components of a bone graft composition or material described herein, such as the phrase "by volume" or "% v/v" refer to the volume fraction of the specified component of the bone graft composition or composition relative to the total volume of the bone graft composition or material. The total volume of the bone graft composition or composition includes the volume of the carrier component.

Particles

The particles used in synthetic bone grafts can be made of a variety of different materials, and each can have a unique resorption rate, porosity, shape, etc. For example, in some embodiments, the materials include α-tricalcium phosphate (α-TCP), β-tricalcium phosphate (β-TCP), hydroxylapatite (HA), and bioactive glass. In such embodiments, each material has a different resorption rate. In order of fastest-to-slowest resorption rate, the exemplary materials are: α-TCP, β-TCP, bioactive glass, and HA. As disclosed herein, the plurality of unique resorption rates provides advantages for the compositions described herein because the unique rates allow for timed resorption of materials to create an ideal environment for bone growth.

The materials are commercially available from vendors such as Berkeley Advance Biomaterials and Mo-Sci Corporation. Common commercial uses for these materials include dental implants, coatings, regenerative medicine, toothpaste, bone void fillers, maxillofacial graft, bone cement, spinal fusion graft, and inner ear ossicle replacement.

Hydroxyapatite (sometimes referred to as hydroxylapatite) (HA) is an essential component in the particles and is required for bone regeneration. HA is present in the particles at about 30 wt. % to about 70 wt. % or more preferably at about 40 wt. % to about 60 wt. % or at about 30 wt. % to about 50 wt. %. HA facilitates bone regeneration through conduction or by serving as a scaffold for filling defects.

In some embodiments, the particles comprise tricalcium phosphate ($Ca_3(PO_4)_2$) (TCP). Generally, TCP facilitates the regrowth of bone at the target repair site. In some embodiments, the TCP is an osteoinductive agent. In some embodiments, the particles comprise one or more specific forms of TCP. In such embodiments, the particle can include 3-tricalcium phosphate at about 30 wt. % to about 50 wt. % and/or α-tricalcium phosphate at about 2.5 wt. % to about 25 wt. %. The unique forms of tricalcium phosphate have a different properties, including, for example, solubility, stability, biodegradability, and resorption rates in a target repair site. In some embodiments, the β-tricalcium phosphate and α-tricalcium phosphate are manufactured in separate particles. In some embodiments, the β-tricalcium phosphate and α-tricalcium phosphate are combined in the same particles.

In some embodiments, the particles further comprise bioactive glass at about 5 wt. % to about 20 wt. %. Bioactive glass is generally biocompatible and can be configured to help form and grow healthy bone. In some embodiments, the bioactive glass is configured to facilitate the regrowth of bone at the target repair site. In some embodiments, the bioactive glass is an osteoconductive agent. Bioactive glass works well for forming bone but resorbs at a rapid rate. For individuals that grow bone at a slower rate (e.g., smokers, diabetics), the synthetic material should be controlled for optimal growth over time regardless of the bone growth rate of the individual. In some embodiments, the bioactive glass can be disposed on, embedded in, or otherwise mixed into a particle comprising hydroxyapatite, β-tricalcium phosphate, and α-tricalcium phosphate.

The bioactive glass can be any alkali-containing ceramic, glass, glass-ceramic, or crystalline material that facilitates bone formation after contact with a biological environment. Suitable examples of bioactive glass include 45S5, 58S, S70C30, S53P4, or a combination of the foregoing bioactive glasses. In some embodiments, the bioactive glass is 45S5 Bioglass, which has a nominal chemical composition of 45% silicon dioxide ($SiO_2$) (±2%), 24.5% calcium oxide (CaO) (±2%), 24.5% sodium oxide ($Na_2O$) (±2%), and 6% phosphorous pentoxide ($P_2O_5$) (±1%). In some embodiments, the bioactive glass includes trace or minimal amounts of at least one heavy element, including, e.g., arsenic (As), cadmium (Cd), mercury (Hg), lead (Pb), or a combination thereof. For example, the bioactive glass can include As in an amount less than about 3 parts per million (ppm); Cd in an amount less than about 5 ppm; Hg in an amount less than about 5 ppm; and/or Pb in an amount less than about 30 ppm. In some embodiments, the bioactive glass is a 45S5. In some embodiments, the bioactive glass further including 3 ppm As, 5 ppm Cd, 5 ppm Hg, and 30 ppm Pb.

The bioactive glass can be in any suitable form. In some embodiments, e.g., the bioactive glass is in particulate form. In the particulate form, the bioactive glass particles are discrete and generally not interconnected. As such, the bioactive glass particles, collectively, are generally amorphous. In other words, the bioactive glass particles, collectively, generally lack an intentional structure or organization. The bioactive glass particles can be generally irregular in shape. In some embodiments, the bioactive glass particles have a smooth surface.

The bioactive glass particles can be any suitable size. In some embodiments, the bioactive glass has a particle size in a range of about 1 micron to about 1000 microns. In some embodiments, at least a portion of the bioactive glass particles are within a range of about 50 microns to about 500 microns. In some embodiments, the bioactive glass includes particles within a range of about 75 microns to about 400 microns. In some embodiments, the bioactive glass includes particles within a range of about 150 microns to about 300 microns. All ranges are inclusive and combinable. In some embodiments, the bioactive glass can include particles of various sizes; for example, of various sizes within at least one of the foregoing ranges. For example, in some embodiments, at least 85% of the bioactive glass are particles within a range of about 212 μm to about 425 μm. Any suitable method of measuring the bioactive glass particle size may be used. For example, the bioactive glass particles, in addition to HA, β-tricalcium phosphate and α-tricalcium phosphate, can be sieved using ASTM sieves according to ASTM E 11 (1995) method. This method permits the retention of bioactive glass particles (or granules) between 40 and 70 mesh. Because particles screened within a certain range may contain a small amount of smaller particles due to screen blinding or stuck in pores of larger particles, a precision screen may be used to determine the amount of particles within the desired particle size range.

Described herein are particles that may be useful in a synthetic bone graft composition for the repair of a bone defect in a mammal. Particle size analysis of the components of each of the particle embodiments described below was performed using a laser diffraction particle size analyzer wherein the measured sample is dispersed in a 50:50 mixture of glycerin:deionized ultra-filtered water to maintain suspension of the particles during analysis.

In some embodiments, the particle is biphasic and comprises hydroxyapatite and β-tricalcium phosphate. The biphasic particle comprises 40 wt. % to about 60 wt. % hydroxyapatite wherein the particle size of the hydroxyapatite ranges from about 2 μm to about 20 μm as determined by scanning electron microscopy and particle size analysis and about 40 wt. % to about 60 wt. % β-tricalcium phosphate wherein the particle size of the β-tricalcium phosphate ranges from about 2 μm to about 20 μm as determined by scanning electron microscopy and particle size analysis. The referenced particle sizes of the hydroxyapatite and β-tricalcium phosphate refer to the sizes of the components prior to sintering.

In some embodiments, the particle is triphasic and comprises about 40 wt. % to about 60 wt. % hydroxyapatite, wherein the particle size of the hydroxyapatite ranges from about 2 μm to about 20 μm as determined by scanning electron microscopy and particle size analysis, about 30 wt. % to about 50 wt. % β-tricalcium phosphate wherein the particle size of the β-tricalcium phosphate ranges from about 2 μm to about 20 μm as determined by scanning electron microscopy and particle size analysis, and about 5 wt. % to about 25 wt. % α-tricalcium phosphate, wherein the particle size of the α-tricalcium phosphate ranges from about 50 μm to about 100 μm as determined by scanning electron microscopy and particle size analysis. The referenced particle sizes of the hydroxyapatite, β-tricalcium phosphate, and α-tricalcium phosphate refer to the sizes of the components prior to sintering.

In some embodiments, the particle is quadphasic and comprises about 40 wt. % to about 60 wt. % hydroxyapatite, wherein the particle size of the hydroxyapatite ranges from about 2 μm to about 20 μm as determined by scanning electron microscopy and particle size analysis, about 30 wt. % to about 50 wt. % β-tricalcium phosphate wherein the particle size of the β-tricalcium phosphate ranges from about 2 μm to about 20 μm as determined by scanning electron microscopy and particle size analysis, about 5 wt. % to about 25 wt. % α-tricalcium phosphate, wherein the particle size of the α-tricalcium phosphate ranges from about 50 μm to about 100 μm as determined by scanning electron microscopy and particle size analysis, and about 5 wt. % to about 20 wt. % bioactive glass, wherein the particle size of the bioactive glass ranges from about 20 μm to about 90 μm as determined by scanning electron microscopy and particle size analysis. The referenced particle sizes of the hydroxyapatite, β-tricalcium phosphate, α-tricalcium phosphate, and bioactive glass refer to the sizes of the components prior to sintering.

Thus, a quadraphasic particle can comprise, for example, about 25 wt %; about 30 wt %; about 35 wt %; about 40 wt %; about 45 wt %; about 50 wt %; about 55 wt %; about 60 wt %; about 65 wt %; or about 70 wt % hydroxyapatite. A quadraphasic particle can comprise, for example, about 25 wt %; about 30 wt %; about 35 wt %; about 40 wt %; about 45 wt %; or about 50 wt % β-tricalcium phosphate. A quadraphasic particle can comprise, for example, about 2 wt %; about 3 wt %; about 4 wt %; about 5 wt %; about 7 wt %; about 10 wt % about 15 wt %; about 20 wt %; about 25 wt %; about 30 wt %; about 35 wt %; about 40 wt %; or about 45 wt % α-tricalcium phosphate. A quadraphasic particle can comprise, for example, about 2 wt %; about 3 wt %; about 4 wt %; about 5 wt %; about 7 wt %; about 8 wt %; about 10 wt % about 15 wt %; about 20 wt %; or about 25 wt % bioactive glass.

A quadraphasic particle can comprise, for example, about 25 wt % hydroxyapatite; about 25 wt % β-tricalcium phosphate; about 25 wt % α-tricalcium phosphate; and about 25 wt % bioactive glass; about 25 wt % hydroxyapatite; about 25 wt % β-tricalcium phosphate; about 45 wt % α-tricalcium phosphate; and about 5 wt % bioactive glass; about 25 wt % hydroxyapatite; about 25 wt % β-tricalcium phosphate; about 5 wt % α-tricalcium phosphate; and about 45 wt % bioactive glass; about 25 wt % hydroxyapatite; about 40 wt % β-tricalcium phosphate; about 20 wt % α-tricalcium phosphate; and about 15 wt % bioactive glass; about 25 wt % hydroxyapatite; about 35 wt % β-tricalcium phosphate; about 10 wt % α-tricalcium phosphate; and about 30 wt % bioactive glass; about 30 wt % hydroxyapatite; about 25 wt % β-tricalcium phosphate; about 15 wt % α-tricalcium phosphate; and about 30 wt % bioactive glass; about 35 wt % hydroxyapatite; about 35 wt % β-tricalcium phosphate; about 15 wt % α-tricalcium phosphate; and about 15 wt % bioactive glass; about 35 wt % hydroxyapatite; about 55 wt % β-tricalcium phosphate; about 5 wt % α-tricalcium phosphate; and about 5 wt % bioactive glass; about 35 wt % hydroxyapatite; about 55 wt % β-tricalcium phosphate; about 5 wt % α-tricalcium phosphate; and about 5 wt % bioactive glass; about 40 wt % hydroxyapatite; about 25 wt % β-tricalcium phosphate; about 5 wt % α-tricalcium phosphate; and about 30 wt % bioactive glass; about 40 wt % hydroxyapatite; about 35 wt % β-tricalcium phosphate; about 15 wt % α-tricalcium phosphate; and about 10 wt % bioactive glass; about 40 wt % hydroxyapatite; about 30 wt % β-tricalcium phosphate; about 25 wt % α-tricalcium phosphate; and about 5 wt % bioactive glass; about 45 wt % hydroxyapatite; about 25 wt % β-tricalcium phosphate; about 15 wt % α-tricalcium phosphate; and about 15 wt % bioactive glass; about 45 wt % hydroxyapatite; about 35 wt % β-tricalcium phosphate; about 15 wt % α-tricalcium phosphate; and about 5 wt % bioactive glass; about 45 wt % hydroxyapatite; about 25 wt % β-tricalcium phosphate; about 5 wt % α-tricalcium phosphate; and about 25 wt % bioactive glass; about 50 wt % hydroxyapatite; about 35 wt % β-tricalcium phosphate; about 5 wt % α-tricalcium phosphate; and about 10 wt % bioactive glass; about 50 wt % hydroxyapatite; about 40 wt % β-tricalcium phosphate; about 5 wt % α-tricalcium phosphate; and about 5 wt % bioactive glass; about 50 wt % hydroxyapatite; about 25 wt % β-tricalcium phosphate; about 5 wt % α-tricalcium phosphate; and about 20 wt % bioactive glass; about 50 wt % hydroxyapatite; about 25 wt % β-tricalcium phosphate; about 20 wt % α-tricalcium phosphate; and about 5 wt % bioactive glass; about 55 wt % hydroxyapatite; about 35 wt % β-tricalcium phosphate; about 5 wt % α-tricalcium phosphate; and about 5 wt % bioactive glass; about 55 wt % hydroxyapatite; about 40 wt % β-tricalcium phosphate; about 2 wt % α-tricalcium phosphate; and about 3 wt % bioactive glass; about 55 wt % hydroxyapatite; about 25 wt % β-tricalcium phosphate; about 15 wt % α-tricalcium phosphate; and about 5 wt % bioactive glass; about 60 wt % hydroxyapatite; about 25 wt % β-tricalcium phosphate; about 10 wt % α-tricalcium phosphate; and about 5 wt % bioactive glass; about 60 wt % hydroxyapatite; about 30 wt % β-tricalcium phosphate; about 5 wt % α-tricalcium phosphate; and about 5 wt % bioactive glass; about 60 wt % hydroxyapatite; about 25 wt % β-tricalcium phosphate; about 7 wt % α-tricalcium phosphate; and about 8 wt % bioactive glass; about 65 wt % hydroxyapatite; about 25 wt % β-tricalcium phosphate; about 2 wt % α-tricalcium phosphate; and about 8 wt % bioactive glass; or about 70 wt % hydroxyapatite; about 25 wt % β-tricalcium phosphate; about 2 wt % α-tricalcium phosphate; and about 3 wt % bioactive glass.

The particles can be any suitable size. In some embodiments, the size of the particles is in a range of about 50 micrometers (μm) to about 2.5 millimeters (mm), or a range of about 250 μm to about 1 mm, or a range of about 300 μm to about 850 μm. In some embodiments, the size of the quadphasic particle is in a range of about 0.1 mm to about 2.0 mm, or about 0.3 mm to about 1.0 mm. The endpoints of all ranges are interchangeable, inclusive, and/or combinable. Generally, larger particles take longer to be absorbed in vivo than smaller particles. As the particle size decreases, more particles can be included in the composition and the total surface area of all particles in the composition increases.

Thus, for example, the quadraphasic particles can be between about 80 μm-850 μm; about 80 μm-850 μm; about 80 μm-2 mm; about 100 μm-2 mm; about 300 μm-1 mm; about 350 μm-2 mm; about 900 μm-2 mm; about 80 μm-850 μm.

Figure 17:
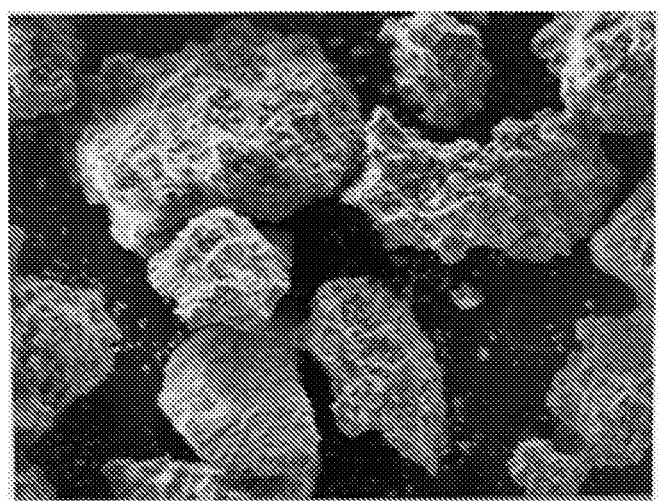
FIG. 17 is an image of an irregularly-shaped particles, in accordance with embodiments disclosed herein.
Figure 18:
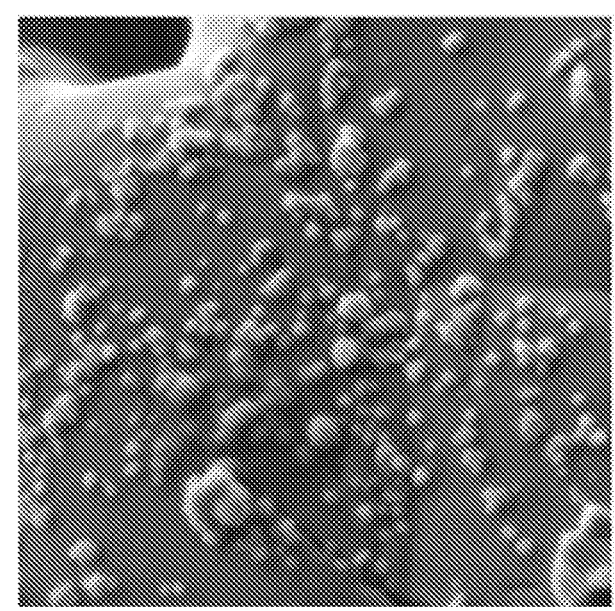
FIG. 18 is an image of a surface texture of a particle, in accordance with embodiments disclosed herein.

The particles can be any suitable shape. For example, the particles can be irregular, spherical, needles, rods, fibers, whiskers, tubular, porous, non-porous, etc. In some embodiments, the particles are spherical. In some embodiments, the particles are irregularly shaped. In some embodiments, the irregular-shaped particles have a larger surface area than spherical particles, therefore providing a greater area for cellular activity and bone growth. For example, as shown in FIG. 17, the particles are non-spherical and irregularly-shaped. FIG. 18 shows the surface texture of a particle. As shown in the image, the surface is not flat and includes several deposits of micro-HA and nano-HA thereon. The surface HA increases the total surface area and roughness of the particle, and therefore enhances the in vivo cellular activity and host reactions on the surface, including an inflammatory response that draws the necessary cells to begin bone formation.

The present invention also contemplates measuring particle size. There are several methods for measuring particle size and particle size distribution (see, e.g., Maaβ et al., Experiments in Fluids. 50 (2): 259-269). Some of them are based on light, other on ultrasound, or electric field, or gravity, or centrifugation. Technology such as dynamic image analysis (DIA) can make particle size distribution analyses much easier. This approach can be seen in instruments like Retsch Technology's CAMSIZER or the Sympatec QUICPIC series of instruments. They still lack the capability of inline measurements for real time monitoring in production environments. Therefore, imaging devices like the SOPAT system (https://sopat.de/en/mesoscopic-probe/) are most efficient.

In all methods the size is an indirect measure, obtained by a model that transforms, in abstract way, the real particle shape into a simple and standardized shape, like a sphere (the most usual) or a cuboid (when minimum bounding box is used), where the size parameter (ex. diameter of sphere) makes sense. Exception is the mathematical morphology approach, where no shape hypothesis is necessary.

Definition of the particle size for an ensemble (collection) of particles presents another problem. Real systems are practically always polydisperse, which means that the particles in an ensemble have different sizes. The notion of particle size distribution reflects this polydispersity. There is often a need for a certain average particle size for the ensemble of particles.

The particle size of a spherical object can be unambiguously and quantitatively defined by its diameter. However, a typical material object is likely to be irregular in shape and non-spherical. The above quantitative definition of particle size cannot be applied to non-spherical particles. There are several ways of extending the above quantitative definition to apply to non-spherical particles. Existing definitions are based on replacing a given particle with an imaginary sphere that has one of the properties identical with the particle.

Volume-based particle size equals the diameter of the sphere that has the same volume as a given particle. Typically used in sieve analysis, as shape hypothesis (sieve's mesh size as the sphere diameter).

$$D = 2\sqrt[3]{\frac{3V}{4\pi}}$$

where
D: diameter of representative sphere
V: volume of particle
Area-based particle size equals the diameter of the sphere that has the same surface area as a given particle. Typically used in optical granulometry techniques.

$$D = \sqrt[2]{\frac{4A}{\pi}}$$

where
D: diameter of representative sphere
A: surface area of particle
In some measures the size (a length dimension in the expression) cannot be obtained, only calculated as a function of another dimensions and parameters Weight-based particle size equals the diameter of the sphere that has the same weight as a given particle. Useful as hypothesis in centrifugation and decantation, or when the number of particles can be estimated (to obtain average particle's weight as sample weight divided by the number of particles in the sample). This formula is only valid when all particles have the same density.

$$D = 2\sqrt[3]{\frac{3W}{4\pi dg}}$$

Formula I where
D: diameter of representative sphere
W: weight of particle
d: density of particle
g: gravitational constant
Hydrodynamic or aerodynamic particle size equals the diameter of the sphere that has the same drag coefficient as a given particle. Another complexity in defining particle size in a fluid medium appears for particles with sizes below a micrometre. When a particle becomes that small, the thickness of the interface layer becomes comparable with the particle size. As a result, the position of the particle surface becomes uncertain.

The method of determining particle size distribution may be by one known to one of skill in the art. For example, a method of determining particle size may be one or more of the following methods, or may be varied by a person of ordinary skill:

Sieve analysis: This continues to be used for many measurements because of its simplicity, inexpensiveness, and ease of interpretation. Methods include simple shaking of the sample in sieves until the amount retained becomes more or less constant. Alternatively, the sample may be washed through with a non-reacting liquid (usually water) or blown through with an air current.

Air elutriation analysis: Material can be separated by means of an elutriator, which consists of a vertical tube up which fluid is passed at a controlled velocity. When the particles are introduced, often through a side tube, the smaller particles are carried over in the fluid stream while the large particles settle against the upward current. Starting with low flow rates, small less dense particles attain terminal velocities, and flow with the stream, the particle from the stream is collected in overflow and hence will be separated from the feed. Flow rates can be increased to separate higher size ranges. Further size fractions can be collected if the overflow from the first tube is passed vertically upwards through a second tube of greater cross-section, and any number of such tubes can be arranged in series.

Photoanalysis: Materials can be analyzed through photoanalysis procedures. Unlike sieve analyses which can be time-consuming and less accurate, taking an image, e.g. photo, of a sample of the materials to be measured and using software to analyze the image can result in rapid, accurate measurements. Another advantage is that the material can be analyzed without being handled.

Optical counting methods: Particle sizes can be measured microscopically by sizing against a graticule and counting, but for a statistically valid analysis, millions of particles must be measured. While this may seem arduous when done manually, there is commercially available equipment to undertake automated analysis of electron micrographs. This is especially useful for determining the particle size within the range of 0.2 to 100 micrometers.

Electroresistance counting methods: An example of this is the Coulter counter, which measures the momentary changes in the conductivity of a liquid passing through an orifice that take place when individual non-conducting particles pass through. The particle count is obtained by counting pulses. This pulse is proportional to the volume of the sensed particle.

Sedimentation techniques. These are based upon study of the terminal velocity acquired by particles suspended in a viscous liquid. Sedimentation time is longest for the finest particles, so this technique is useful for sizes below 10 μm, and measurements as to sub-micrometer particles may be impacted by the effects of Brownian motion. Typical apparatus disperses the sample in liquid, then measures the density of the column at timed intervals. Other techniques determine the optical density of successive layers using visible light or x-rays.

Scanning electron microscopy: This method involves scanning the surface of the sample area with a beam of electrons, which interact with the sample to provide information regarding the topography of the sample. The most common scanning electron microscopy methods rely on the detection of secondary electrons emission through the interaction of the primary electron beam with the atoms of the sample. The resolution of scanning electron microscopy can be well below that of 1 nm. Scanning electron microscopy requires a high vacuum and can be expensive.

Laser diffraction methods: These depend upon analysis of the "halo" of diffracted light produced when a laser beam passes through a dispersion of particles in air or in a liquid. The angle of diffraction increases as particle size decreases, so that this method is particularly good for measuring sizes between 0.1 and 3,000 μm. Advances in sophisticated data processing and automation have allowed this to become a dominant method used for particle size determination. This technique is relatively fast and can be performed on very small samples. A particular advantage is that the technique can generate a continuous measurement for analyzing process streams. Laser diffraction measures particle size distributions by measuring the angular variation in intensity of light scattered as a laser beam passes through a dispersed particulate sample. Large particles scatter light at small angles relative to the laser beam and small particles scatter light at large angles. The angular scattering intensity data is then analyzed to calculate the size of the particles responsible for creating the scattering pattern, using the Mie theory of light scattering. The particle size is reported as a volume equivalent sphere diameter. Particle size analysis of the particles described herein was performed using a laser diffraction particle size analyzer wherein the measured sample is dispersed in a 50:50 mixture of glycerin:deionized ultra-filtered water to maintain suspension of the particles during analysis.

Laser Obscuration Time (LOT) or Time Of Transition (TOT): A focused laser beam rotates in a constant frequency and interacts with particles within the sample medium. Each randomly scanned particle obscures the laser beam to its dedicated photo diode, which measures the time of obscuration. The time of obscuration directly relates to the particle's Diameter, by a simple calculation principle of multiplying the known beam rotation Velocity in the directly measured Time of obscuration, $(D=V*t)$.

Acoustic spectroscopy or ultrasound attenuation spectroscopy: Instead of light, this method employs ultrasound for collecting information on the particles that are dispersed in fluid. Dispersed particles absorb and scatter ultrasound similarly to light. It turns out that instead of measuring scattered energy versus angle, as with light, in the case of ultrasound, measuring the transmitted energy versus frequency can provide better measurement. The resulting ultrasound attenuation frequency spectra are the raw data for calculating particle size distribution. It can be measured for any fluid system with no dilution or other sample preparation. Calculation of particle size distribution is based on theoretical models that are well verified for up to 50% by volume of dispersed particles. However, this technique has limitations including as particle sizes approach the nanoscale.

Tables 1-3 show compositions of embodiments of a biphasic, triphasic, and quadphasic particle respectively:

TABLE 1

| Component | Wt. % | Size |
|---|---|---|
| Hydroxyapatite | 40-60% | About 2-20 μm |
| β-tricalcium phosphate | 30-50% | About 2-20 μm |

TABLE 2

| Component | Wt. % | Size |
| --- | --- | --- |
| Hydroxyapatite | 40-60% | About 2-20 μm |
| β-tricalcium phosphate | 30-50% | About 2-20 μm |
| α-tricalcium phosphate | 5-25% | About 50-100 μm |

TABLE 3

| Component | Wt. % | Size |
| --- | --- | --- |
| Hydroxyapatite | 40-60% | About 2-20 μm |
| β-tricalcium phosphate | 30-50% | About 2-20 μm |
| α-tricalcium phosphate | 5-25% | About 50-100 μm |
| Bioactive glass | 5-20% | About 20-90 μm |

Methods of Making the Particles

In some embodiments, the individual particle components are sintered together to form a single particle. In some embodiments, the sintering temperature is in a range of about 500° C. to about 1700° C. In other embodiments the sintering temperature is in a range of about 900° C. to about 1300° C. For example, in some embodiments, the sintering temperature is about 1100° C. In some embodiments, the sintering temperature is relevant to the properties of the bone graft composition because an elevated temperature can assist in the formation of a physical bond between the individual components. Sintering time is also a relevant factor. In some embodiments, the particles are sintered for about 30 minutes to about 6 hours. In some embodiments, the bond strength relates to the firmness of the particle, which can be significant with respect to the effectiveness of the bone graft composition. In some embodiments, the level of firmness effects the handling of the bone graft composition, as well as the absorption rate of the particles after delivery to the body. Each component resorbs at a different rate in the body, which can be utilized for controlling the rate of bone growth over time. In some embodiments, the particle components are prepared as a homogeneous mixture so the resulting composition contains a consistent scaffolding and bioactivity distribution throughout.

Each component is weighed before mixing. The particles can be made by adding hydroxyapatite, α-tricalcium phosphate, β-tricalcium phosphate, and bioactive glass individually and mixing together until homogenous. This process may take 15 minutes to 6 hours. The individual particles may be mixed by hand or machine. The material must be mixed continuously until the material is evenly distributed. This will ensure each particle will have four phases of resorption for a quadphasic particle. A triphasic particle can be made using three out of the four components, and a biphasic particle can be made using two out of the four components. A pore forming agent may optionally be added to create the optimal porosity desired. Once evenly distributed the material may be compressed and sintered to bind the material. Once the material is bound together or formed into sintered particles, the size of the sintered particles may be adjusted, e.g., by being broken into smaller pieces or particles (e.g., via pulverizer, mortar and pestle), and/or by being sieved, to obtain particles of the desired size of this invention and/or for use in compositions or formulations of the invention.

In some embodiments, a quadphasic particles may be manufactured in various way to ensure the quadphasic components are preserved and expressed. The finished particle may be made from mixing very small particles under 30 microns together homogenously. Then these particles may be sintered at a high temperature to achieve bonding and tensile strength. In some embodiments, a quadphasic particle may all be achieved by mixing HA and β-TCP together at high temperatures and then sintered. This will make a biphasic particle. Then the bioactive glass and α-TCP may be dusted on the outside of the particle and heated for bonding. This may be beneficial to ensure integrity of particle is strong enough to withstand a high tensile load.

Bone Graft Compositions

In various embodiments, a bone graft composition (or material) for bone graft procedures is provided. A bone graft composition in which all of the components are fused into a biphasic, triphasic, or quadphasic particle would improve controlled distribution of each component and the stability of the composition as a whole. This is particularly the case when the composition is delivered in a minimally invasive procedure. In some embodiments, the bone graft composition is configured to facilitate repair or regeneration of bone at a target repair site. For example, in some embodiments, the bone graft composition can be osteoconductive, osteoinductive, osteogenic, or any combination thereof. The target repair site can be, for example, a void, gap, or other defect in a bone or other bony structure in the body of a patient. For example, the bone graft composition can be configured to facilitate bone growth at a target repair site in the spine, pelvis, mouth (dental), an extremity, the cranium, or another bone or bony structure in the patient's body. The bone graft composition is configured to be implanted or otherwise directed to the target repair site. For example, in some embodiments, the bone graft composition is configured to be implanted or deposited at the target repair site in a non-load bearing application.

The bone graft compositions disclosed herein can include modifications in surface topography in order to provide increase the osteoconductivity of the surface. Such modifications can be directed to increasing cell adhesion, for example, adhesion of mesenchymal stem cells and osteoblasts, cell growth, and cell differentiation. Exemplary modifications can include modifications of surface electrical charge and surface topography. Negative electrical charges and calcium phosphate surface coating and textures can be added to provide suitable adhesion surface for osteocytes (bone forming cells). These coatings/texturing can be added in a variety of ways, for example, by preparing a slurry of HA, β-tricalcium phosphate, α-tricalcium phosphate, bioactive glass or other material suitable for bone growth and sintering to the primary particle, or by sintering nano or micro sized particles into the primary particle, or by preparing a slurry of osteoconductive material and letting it dry on the primary particle. An exemplary method is to mix the nano, micro or sub-micron HA into the primary particle and sinter the material together leaving behind an optimal surface texturing for osteocyte attachment.

In some embodiments, the bone graft composition comprise a hydroxyapatite (HA) substrate having submicron-HA, micro-HA, and/or nano-HA surface structures. Submicron-HA, micro-HA, and nano-HA particles have a fine flour-like texture that can be used in a bone graft putty or powder to modify the consistency of the bone graft composition. In such embodiments, the submicron-HA, micro-HA, or nano-HA can be disposed on, embedded in, or otherwise mixed into the particle. In such embodiments, the submicron-HA, micro-HA, or nano-HA can be sintered or non-sintered The submicron, micron, or nano HA surface structures may serve as a cell attachment area to stimulate osteogenesis. The HA or multiphasic particles may contain sub-micron, nano, or micron porosity that allows for angiogenesis, which is essential for bone growth. These pores allow the particle to vascularize and stimulate cell proliferation. Submicron-HA, nano-HA, and/or micro-HA surface structures can increase the surface area and roughness of a particle in a bone graft composition, and therefore enhance the in vivo cellular activity and host reactions near the composition, including an inflammatory response that draws the necessary cells to begin bone formation at the target repair site. In such embodiments, nano-HA, submicron-HA, and/or micro-HA can accelerate the wound healing process. It must be recognized, however, too much micro-HA, submicron-HA, or nano-HA can cause an adverse effect, lead to fibrotic tissue formation, or result in a lack of bone growth. Accordingly, a suitable amount of micro-HA, submicron-HA, and/or nano-HA is required, wherein the suitable amount is a quantity that stimulates cellular activity and host reactions without causing serious adverse effects. In some embodiments, the size of the micro-HA, submicron-HA, or nano-HA is about 50 nanometers (nm) to about 100 micrometers ("microns") (μm) prior to sintering. In some embodiments, the size of the micro-HA/nano-HA is about 20 nm to about 50 μm, or about 5 μm to about 35 μm following sintering. Thus, micro-HA/nano-HA can be about 20 nm, about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, or about 100 nm.

In some embodiments, the bone graft composition comprises bioactive glass. The bioactive glass can be mixed with the carrier such that the bioactive glass is randomly dispersed throughout. Bioactive glass works well for forming bone but resorbs at a rapid rate. For individuals that grow bone at a slower rate (e.g., smokers, diabetics), the synthetic material should be controlled for optimal growth over time regardless of the bone growth rate of the individual. For example, the bioactive glass can be mixed with a carrier to form a substantially homogenous mixture (e.g., a slurry). In some embodiments, the bioactive glass can be disposed on, embedded in, or otherwise mixed into a particle comprising hydroxyapatite, β-tricalcium phosphate, and α-tricalcium phosphate. In some embodiments, the bioactive glass is disposed on (e.g., coated or sprinkled onto) a surface of the composition. In some embodiments, the bioactive glass is present at about 1 wt. % to about 30 wt. %.

In some embodiments, the bone graft composition comprises a biphasic, triphasic, or quadphasic particle, and a carrier. The added particle carrier has many benefits such as helping with handling, flowability, cohesiveness, texturing, wicking, bonding, shaping, handling, packaging, stimulating bone growth, expanding, hardening, and/or other benefits. In some embodiments, the carrier comprises a single component. In some embodiments, the carrier comprises a plurality of components. The carrier or components thereof can be included in any suitable amount. For example, the amount of carrier may be from about 0.5% to about 80% w/w, or about 1% to about 70%, or about 10% to about 60%, etc. The endpoints of all ranges are interchangeable, inclusive, and/or combinable. The carrier can have any suitable viscosity. In some embodiments, for example, the carrier comprises a component for increasing the flowability of the composition. In some embodiments, the carrier comprises a thickener that prevents separation of the composition.

Carrier compounds such as polyethylene glycol and glycerol are commercially available from vendors such as Millipore Sigma, Thermo Fisher Scientific, Promega, E&C Chemicals, and ProChem.

In some embodiments, the carrier comprises a bioresorbable polymer. Over time, a bioresorbable polymer is safely absorbed by the body, and leaves behind no foreign material. The bioresorbable polymer can be, for example, a polyol or an aliphatic polyether. The bioresorbable polymer can include linear or branched alkyl chains. In some embodiments, the bioresorbable polymer comprises homopolymers, copolymers, and graft copolymers that contain ether linkages in their main polymer chain structure. In some embodiments, the bioresorbable polymers are derived from monomers that are vicinal cyclic oxides, or epoxides, of aliphatic olefins, such as ethylene, propylene, and butylene.

Bioresorbable polymers have a range of suitable molecular weights. Lower molecular weight polyether polymers are generally liquids, increasing in viscosity with molecular weight. High molecular weight polyether polymers can be thermoplastic. The solubility of polyether polymers range from hydrophilic water soluble polymers that are principally derived from ethylene oxide, to hydrophobic, oil-soluble polymers of propylene oxide and butylene oxide.

In some embodiments, the carrier comprises a polyethylene glycol (PEG) polymer, which is polyglycol derived from ethylene glycol, represented by the formula $H(OCH_2CH_2)_nOH$, in which n represents the average number of oxyethylene groups. In some embodiments, the PEG has a molecular weight of about 100-10,000,000 grams/mole, or about 500-10,000 grams/mole, or about 1,000-5,000 grams/mole, or about 1,500-3,000 grams/mole. In some embodiments, the PEG has a molecular weight that is less than 20,000 grams/mole. The endpoints of all ranges are interchangeable, inclusive, and/or combinable.

Thus for example, the PEG can have a molecular weight of about 1500 g/mole; about 1800 g/mole; about 2000 g/mole; about 2500 g/mole; or about 3800 g/mole.

In some embodiments, the carrier comprises polyvinylpyrrolidone, polyvinyl alcohol, a cellulosic ester or derivative thereof, such as hydroxypropyl methylcellulose, carboxy methylcellulose, and ethylcellulose; pectin, food-grade texturizing agent, gelatin, dextran, collagen, starch, hydrolyzed polyacrylonitrile, hydrolyzed polyacrylamide, polyelectrolyte such as polyacrylic acid salt, etc. Such components can be used to adjust the viscosity of the composition. Methylcellulose, for example, is a non-toxic, non-allergenic, and biodegradable polymer that improves the flowability of the bone graft composition. The methylcellulose or methylcellulose derivatives can have any suitable viscosity. For example, in some embodiments, the viscosity of the methylcellulose or methylcellulose derivatives can be in a range from about 15 centipoise (Cp) to about 4000 Cp (a higher Cp equates to the thicker viscosity). In some embodiments, the methylcellulose is a dry powder. In such embodiments, the dry methylcellulose powder can be mixed with the synthetic materials discussed above and, optionally, additional components such as allograft bone, cancellous bone, and demineralized cortical bone. In some embodiments, a mixture of methylcellulose and other materials may be a dry power capable of being hydrated at the point of use. In some embodiments, the mixture of methylcellulose and other materials may be hydrated during the manufacturing process. In such embodiments, the mixture may be pre-packed in delivery device and ready for use. Methylcellulose can be purchased from commercial sources. Methylcellulose and the quadphasic particles can be mixed together in a dry mix. The dry mix can be rehydrated with saline, blood, bone marrow aspirate, stem cells, platelet rich plasma or radiopaque dye to produce a flowable putty that can be pushed through needles, cannulas or packed into an implant.

In some embodiments, the composition further comprises saline, water, blood, bone marrow aspirate (BMA), etc. In some embodiments, the composition allows for the wicking up of growth factors and cells to assist in fusion. In some embodiments, the bone components contain scaffolding and bone morphogenetic proteins (BMP) that are responsible for osteoinductivity and signaling cells for bone growth. The components can be any suitable size and shape necessary to achieve improved results. In some embodiments, compositions comprising less carrier and more synthetic components and bone components will result in better fusion with the patient's body. In such embodiments, the carrier resorbs quickly while the particles remain at the target site for bone growth. In some embodiments, The dry methylcellulose is mixed with the synthetic materials discussed above and, optionally, allograft bone, cancellous or cortical bone/demineralized cortical bone. This formulation may be packaged in a sterile dish, bowl, syringe, elongated tube, or other device acceptable for mixing. Saline, water, blood, BMA, etc. is then added to the formulation to obtain a moldable and flowable putty. In some embodiments, such a dry formulation allows for the wicking up of growth factors and cells to assist in fusion.

In some embodiments, the carrier comprises an additional polyhydroxy compounds (polyols) and their esters, polysaccharides, surface active agents, and mixtures thereof. Specific examples include glycerol and its monoesters and diesters derived from low molecular weight carboxylic acids, e.g., monoacetin and diacetin (respectively, glycerol monoacetate and glycerol diacetate), ethylene glycol, diethylene glycol, triethylene glycol, 1,2-propanediol, trimethylolethane, trimethylolpropane, pentaerythritol, sorbitol, and the like. The additional polyol can be included in any suitable amount. Preferably, the polyol is present in the carrier in an amount between about 40 wt. % and 60 wt. % of the carrier.

In some embodiments, the carrier comprises one or more of the following: PEG, glycerol, methylcellulose, poly(alkylene glycol), collagen, pentaerythritol, dipentaerythritol, tripentaerythritol, 1,2,4-butanetriol, trimethylolpropane, 1,2,3-trihydroxyhexane, myo-inositol, ascorbic acid, a saccharide, poly(caprolactones), poly(lactide), poly(glycolide), polyglyconate, poly(arylates), poly(anhydrides), poly(hydroxy acids), polyesters, poly(ortho esters), polycarbonates, poly(propylene fumarates), poly(propylene glycol-co fumaric acid), polyamides, polycaprolactone (PCL), polyesters, polyethers, polyureas, polyamines, polyamino acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxybutyrate/valerate copolymers, poly(vinyl pyrrolidone), polycyanoacrylates, polyurethanes, water, bone marrow aspirate, saline, blood, platelet rich plasma, carboxymethylcellulose, lecithin, polysaccharides or sugar alcohols (e.g., mannitol, xylitol, sorbitol, etc.). For example, in some embodiments the carrier comprises PEG and glycerol. In such embodiments, the carrier includes about 25-75 wt. % glycerol and about 25-75 wt. % PEG (a ratio of about 0.3 to about 3.0); or about 35-50 wt. % glycerol and about 50-65 wt. % PEG (a ratio of about 0.5 to about 1.85); or about 40-60 wt. % glycerol and about 40-60 wt. % PEG (a ratio of about 0.7 to about 1.5). Each component may be used in varying amounts to adjust the physical, chemical, or biological characteristics of the bone graft.

Thus, for example, the bone graft composition can include about 15 wt % about 16 wt %; about 17 wt %; about 18 wt %; about 19 wt %; about 20 wt %; about 21 wt %; about 22 wt %; about 23 wt %; about 24 wt %; about 25 wt %; about 26 wt %; about 27 wt %; about 28 wt %; about 29 wt %; about 300 wt %; about 35 wt %; or about 40 wt % of PEG carrier.

Thus, for example, the bone graft composition can include about 15 wt % about 16 wt %; about 17 wt %; about 18 wt %; about 19 wt %; about 20 wt %; about 21 wt %; about 22 wt %; about 23 wt %; about 24 wt %; about 25 wt %; about 26 wt %; about 27 wt %; about 28 wt %; about 29 wt %; about 300 wt %; about 35 wt %; or about 40 wt % of glycerol carrier.

In some embodiments, the bone graft composition can include a total carrier amount, for example, a combination of PEG and glycerol, of about 35 wt % about 40 wt %; about 45 wt %; about 50 wt %; about 55 wt %; or about 60 wt %.

In some embodiments, the carrier comprises methylcellulose. The methylcellulose can comprise between about 10 wt % to about 50 wt % of the bone graft composition. Thus, for example, the bone graft composition can include about 10 wt %; about 15 wt %; about 20 wt %; about 25 wt %; about 30 wt %; about 35 wt %; about 40 wt %; about 45 wt %; or about 50 wt % In some embodiments, the bone graft composition can include between about 30 wt % to about 50 wt %; about 35 wt % to about 50 wt %; about 40 wt % to about 45 wt %; about 30 wt % to about 45 wt %; about 30 wt % to about 40 wt %; about 35 wt % to about 50 wt %; about 35 wt % to about 45 wt %; or about 35 wt % to about 40 wt % methylcellulose.

In some embodiments, the carrier comprises a small organic compound or a plurality of small organic compounds comprising from about 25 wt. % to about 75 wt. % of the carrier. For example, in some embodiments, the carrier comprises a small organic compound capable of activating the CB1 and/or CB2 cannabinoid receptors. The CB2 receptor is expressed in osteoblasts and osteoclasts, stimulates bone formation, and inhibits bone resorption. In some embodiments, for example, the cannabinoid is cannabidiol (CBD) or a derivative thereof. The CBD may be in liquid or solid form, which may contribute to improved handling and flowability of the composition.

In some embodiments, collagen is added to the bone graft composition to increase bone growth and handling properties. Collagen may make up between about 15 wt. % to about 60 wt. % of the total weight of the bone graft composition. The triple helical structure of collagen prevents degradation of the protein by enzymes, enables cell adhesion, and participates in proper assembly of the extracellular matrix. In some embodiments, the collagen can be type I collagen, type II collagen, type III collagen, type IV collagen, and/or type V collagen. Collagen may be sourced, for example, from a bovine, avian, porcine, marine animal, or plants. The collagen may in particle, powder, pellet, nanoparticle, nanosphere, fiber, film, sponge, gel, dehydrated, lyophilized, hydrogel, sheet, or disc form. In some embodiments, the collagen is osteoconductive. In some embodiments, the collagen may be mixed with the particles of the bone graft composition and lyophilized. Freeze dried bone grafts can be hydrated and wick up various fluids such as bone marrow aspirate, platelet-rich plasma, blood, or saline. Once hydrated, the bone graft composition has a putty consistency with good handling characteristics. In some embodiments, the fluid used for rehydration can be selected give the bone graft various properties to help stimulate bone growth.

In some embodiments, the bone graft composition includes additional materials. For example, the bone graft material can include autologous bone, allograft bone, or a mixture of the two. In some embodiments, the bone graft material is mixed with a pharmaceutical drug for treating pain, inflammation, infection, etc. The formulation may further include a radiopaque dye or other alternative(s) for enhancing the visualization of the target site during imaging (e.g., fluoroscopy) or during minimally invasive surgery. During such minimally invasive surgeries, the user (e.g., physician) is unlikely to be able to directly visualize where the graft is dispensing because of the patient's muscle, skin, etc.

In some embodiments, the bone graft composition comprises demineralized bone matrix (DBM) cortical bone to increase handling and bone growth properties. DBM cortical bone can also increase in bone morphogenetic proteins, making it osteoinductive. DBM cortical bone has a high content of bone morphogenetic proteins (BMP), including, e.g., BMP-2 and BMP-7, which have bone regenerative properties. DBM cortical bone also handles, flows, and wicks fluid well. In some embodiments, a formulation of DBM cortical bone is mixed with a controlled amount of quadphasic particles of bioactive glass, $\alpha$-TCP, $\beta$-TCP, and HA. In such embodiments, the DBM particles or fibers can have a particle size in the range of about 100 microns to about 1.2 millimeters, or from about 200 microns to about 800 microns, or from about 250 microns to about 750 microns. The endpoints of all ranges are interchangeable, inclusive, and/or combinable. Further, the particle size is important to the flowability of the bone graft and also for inducing bone growth through a high amount of BMPs, which recruit other cells for bone growth. In some embodiments, the composition can be freeze-dried and then reconstituted at the time of use (e.g., surgery), or it can be hydrated during manufacturing to provide a ready-to-use composition. In some embodiments, reconstituting at the time of use with bone marrow aspirate, platelet-rich plasma, stem cells, or blood can improve the osteogenic properties of the bone graft. In some embodiments, the DBM cortical bone is premixed with the quadphasic particles in, e.g., vials, syringes, or elongate tubes. In some embodiments, the DBM cortical bone is mixed on the surgical table at the time of surgery.

The DBM cortical bone can be mixed with the synthetic bone graft compositions at varying concentrations. In some embodiments, a higher concentration of DBM cortical bone provides a higher level of osteoinductivity and better handling characteristics. In some embodiments, after hydration, the bone graft composition comprises DBM cortical bone in a range of about 10% to about 90% by weight, or in a range of about 20% to about 80% by weight. In some embodiments, as shown in Table 4, after hydration, the composition comprises synthetic bone graft material, namely the particles and carrier, in a range of about 10% to about 90% by weight, or in a range of about 20% to about 80% by weight. In some embodiments, the bone graft composition comprises about 40% to about 60% by weight of DBM cortical bone and about 40% to about 60% by weight of synthetic bone graft material. In some embodiments, the bone graft composition comprises about 20% to about 40% by weight of DBM cortical bone and about 60% to about 80% by weight of synthetic bone graft material. The endpoints of all ranges are interchangeable, inclusive, and/or combinable.

In some embodiments, for example, when demineralized cortical bone is mixed with the synthetic bone graft compositions at varying concentrations, it is more beneficial to measure components by volume. Measuring components by weight may not be appropriate because the density of synthetic bone graft materials and allografts can vary greatly. For example, when measuring by weight, a material with high density may comprise a high percentage of the overall weight, but represent a very small volume. This can also be important when mixing bone graft materials with carriers (e.g., PEG, glycerol, methylcellulose, water) because carriers are often rapidly absorbed in the body (e.g., within weeks). When using such a composition, there may be only a few dense particle inside the bone void after a few weeks and a relatively large amount of empty space. Therefore, in some embodiments, as shown in Table 4, the bone graft composition comprises DBM cortical bone in a range of about 15% v/v to about 45% v/v, synthetic bone graft material in a range of about 5% v/v to about 20% v/v, and a carrier in a range of about 45% v/v to about 75% v/v. In some embodiments, the bone graft composition comprises allograft in a range of about 10% v/v to about 50% v/v, synthetic bone graft material in a range of about 5% v/v to about 35% v/v, and a carrier in a range of about 30% v/v to about 80% v/v. The percentages are calculated after hydration has occurred (e.g., during manufacturing or at the point of use). The synthetic bone graft, allograft, and carrier in such embodiments may be any of those herein.

TABLE 4

| Exemplary embodiment | DBM | Synthetic bone graft material | Carrier |
|---|---|---|---|
| 1 | 10-90% w/w | 10-90% w/w | —* |
| 2 | 20-80% w/w | 20-80% w/w | —* |
| 3 | 40-60% w/w | 40-60% w/w | —* |
| 4 | 20-40% w/w | 60-80% w/w | —* |
| 5 | 15-45% v/v | 5-20% v/v† | 45-75% v/v |
| 6 | 10-50% v/v | 5-35% v/v† | 30-80% v/v |

*The indicated percent w/w in the synthetic bone graft material column includes the weight fraction of the carrier.
†The indicated percent v/v in the synthetic bone graft material column excludes the volume fraction of the carrier.

In some embodiments, the composition may also include a biphasic HA and $\beta$-TCP particle sintered and bonded together and separate $\alpha$-TCP and bioactive glass particles for a synergistic effect. This may allow the $\beta$-TCP and HA particles to resorb slower and the $\alpha$-TCP and bioactive glass particles to resorb quicker. This may allow for rapid bone formation initially and create greater porosity once the $\alpha$-TCP and bioactive glass particles resorb. The composition may also have individual particles of $\alpha$-TCP, $\beta$-TCP, bioactive glass, and HA floating around separately. The components may not be sintered together and all separate in the composition, which would not be optimal for controlled resorption within each particle. However, this lack of sintering of the components may be necessary if optimal sintering cannot be achieved.

In some embodiments, the particles of the bone graft composition are porous; i.e., the particles of the bone graft composition contain cavities, channels, and/or interstices that are deeper than they are wide. The particles can have any suitable porosity, wherein porosity is defined as the ratio of the total pore volume to the apparent volume of the particle.

Porosimetry techniques such as mercury intrusion porosimetry can be used to determine various quantifiable aspects of a material's porous nature, such as pore diameter, total pore volume, surface area, and bulk and absolute densities. Mercury intrusion porosimetry employs a pressurized chamber to force mercury into the pores of a porous substrate, filling the larger pores first as pressure is applied and filling the smaller pores upon an increase in the applied pressure. Based on the applied pressure, the surface tension of mercury, and the contact angle of mercury on the sample, the pore diameter can be determined using the Washburn equation:

$$d_p = \frac{4 \cdot \sigma}{p} \cos\theta \qquad \text{Formula II}$$

Where:

$p$ = applied pressure in Pa $d_p$ = pore diameter in m $\sigma$ = surface tension of mercury in N/m $\theta$ = contact angle of mercury on the sample in degrees In some embodiments, the particles comprise a porosity in a range of about 40% to about 95%; or from about 70% to about 85%, or from about 45% to about 80%, or from about 50% to about 65%. In some embodiments, the total porosity is not more than, for example, 55% or 53%.

The pores can have any suitable shape. In some embodiments, for example, the pores have a geometric shape such as a cylinder, cone- or funnel-shape, slit-shape, or ink bottle shape. The pores can be any suitable size. In some embodiments, the particles include micropores, mesopores, and/or macropores. A micropore has a width that does not exceed about 2 nm. A mesopores has a width between about 2 nm and 50 nm. A macropore has a width exceeding about 50 nm (0.05 μm).

In some embodiments, the porosity of the particles of the bone graft composition can be increased as determined by porosimetry techniques. The particles include macropores in the size range of 100-500 μm. These macropores are important for bone growth as they permit tissue ingrowth and bone and blood vessel formation. The particles may also contain mesopores in the size range of 10-100 μm. The mesopores are important to aid in cell adhesion and optimal material degradation.

In some embodiments, the bone graft composition comprises larger particles with increased pore sizes. Such embodiments may be necessary for bone regeneration in areas that are difficult to fuse. Larger particles have a greater surface area and resorb at a slower rate due to greater material density. In some embodiments, the particles can range from about 1-2 mm and may be mixed with any combination of the aforementioned particles. In some embodiments, the particles are not mixed. In some embodiments, the particles may have pores sized between about 100 microns to about 1000 microns. In some embodiments, the pores are surface pores or they are interconnected within the particle, which provides additional area for vascular ingrowth and cell attachment. Particles sized from about 1-2 mm may be added in various amounts (e.g., mass, volume) relative to the total amount of the particles. For example, in some embodiments, a mixture of 500 micron particles and 1000 micron particles can be included in 50:50 ratio. In some embodiments, a mixture of 500 to 1000 micron particles and 1 to 2 mm particles can be included in a 50:50 ratio. Such combinations are not limited. In some embodiments, the overall porosity can range from about 50% to about 90%.

In FIG. 17, for example, a microscopic image of particles comprising hydroxyapatite, β-tricalcium phosphate, α-tricalcium phosphate, and bioactive glass is provided. In FIG. 17, each of the particles is highly porous, which increases the overall surface area available for cell attachment, as well as bone growth in and around the particles. The total surface area of a porous particle includes both the internal surface and external surface areas. The internal surface is the area associated with pores (i.e., the area of the pore walls). The external surface is the area for the outer boundary of the particle, taking into account the roughness of the particle (e.g., cavities that are wider than they are deep).

In some embodiments, the particles in the bone graph composition aggregate close together. In such embodiments, the particles are separated from each other by a small void (i.e., interparticle pore). In such embodiments, it is necessary to distinguish between the intraparticle pores and the interparticle pores. Generally, internal pores are smaller, in terms of size and volume, than the interparticle pores. In such embodiments, the smaller internal pores may nevertheless provide the dominant contribution to the surface area of the composition. In some embodiments, the particles are not packed close together in the bone graph composition. In such embodiments, the particles may be evenly distributed throughout the bone graft composition. In such embodiments, the interparticle pores are evenly distributed or substantially evenly distributed.

In some embodiments, the particle composition, size, and porosity can be adjusted to provide a controlled absorption profile, resulting in an improved bone ingrowth and remodeling. For example, in some embodiments, the particles are evenly distributed throughout the bone graft composition, which can lead to controlled resorption of the particle components during/after a bone graft procedure. In some embodiments, the total porosity can be adjusted. For example, in some embodiments the intraparticle porosity of individual particles and/or the interparticle porosity between particles is adjusted. In some embodiments, the interparticle porosity supports bone formation, and the intraparticle permits the penetration of fluids and vascularization needed for bone maintenance. In some embodiments, the size of the pores, or the distribution of sizes, is adjusted. For example, in some embodiments, the ratio of microporosity, mesoporosity, and macroporosity is adjusted. In some embodiments, the particles are porous and quadphasic (hydroxyapatite, β-tricalcium phosphate, α-tricalcium phosphate, and bioactive glass). In some such embodiments, when there is a high level of porosity, a higher content of HA can be utilized to increase the strength of the particle (i.e., to offset any lost strength resulting from the increased porosity). In some embodiments, smaller sizes of the raw materials can be used at to increase the strength of the particle. In some embodiments, the overall porosity, including micropore and macropores, is from about 50% to about 90%. In some embodiments, the micropore to macropore ratio can range from about 1:2 to about 2:1. In some embodiments, only micropores or only macropores are present. In various embodiments, the pores range from about 10 microns to about 500 microns. In some embodiments, the pores are interconnected from within the particle and/or the non-connected surface pores. In some embodiments, the target location for the implant determines the desired overall porosity, interconnected porosity, particle size, and/or pore size.

In some embodiments, the composition or components thereof are radiopaque. In such embodiments, for example, the β-tricalcium phosphate and/or α-tricalcium phosphate are radiopaque. In some embodiments, the bioactive glass or hydroxyapatite is radiopaque. The components, either alone or combined as the bone graft composition, may be used for minimally invasive graft delivery procedures to visualize bone graft under the skin in situ. In some embodiments, the carrier may provide additional radiopacity. Multiphase particles (e.g., quadphasic particles) are generally radiopaque, but in some cases require enhancements depending on the size of the patient and/or the anatomical region requiring the graft. For instance, methylcellulose or other carrier materials may possess radiopaque properties naturally or via the addition of iodine, Iopamidol, omnipaque, isovue, or another medical-based contrast agent or material with high density used to enhance imaging. In such embodiments, the carrier may be used to wick up iodine or other contrast agents and retain those agents until implanted and then resorbed. The radiopacity of the bone graft composition can be important when used in a minimally invasive posterolateral lumbar fusions. In such procedures, a rasp is used with the graft delivery system. In particular, the bone graft composition is loaded into an elongate tube and placed in the rasp. The delivery system then pushes the bone graft composition out of the hole in the rasp to the area decorticated on the transverse processes. The hold in the rasp will ensure the graft is dispensed in a precise and controlled manner over the decorticated area. During this type of minimally invasive procedure, the bone graft cannot be seen and the surgeon must rely on the radiopacity of the bone graft composition. In such embodiments, the grafts can be seen using x-ray or fluoroscopy to ensure the bone graft is distributed in the desired region. Existing bone graft compositions (synthetic and allograft) fail to provide an adequate level of radiopacity to truly where the graft is being placed using x-ray, CT scan, or fluoroscopy.

In some embodiments, the bone graft composition contains about 30 wt. % to about 70 wt. % of a triphasic particle comprising hydroxyapatite, β-tricalcium phosphate, and α-tricalcium phosphate. In some embodiments, the bone graft composition comprises about 30 wt. % to about 70 wt. % of a carrier, such as PEG and/or glycerol. In some embodiments, the bone graft composition comprises about 1 wt. % to about 30 wt. % bioactive glass. The composition of such an embodiment is shown in Table 5. In some embodiments, the bioactive glass includes particles within a range of about 1 microns to about 1000 microns. In some embodiments, the bioactive glass includes particles within a range of about 75 microns to about 400 microns. In some embodiments, the bioactive glass includes particles within a range of about 150 microns to about 300 microns. All ranges are inclusive and combinable. In some embodiments, the particles of the bone graft composition comprise about 25 wt. % to about 75 wt. % of hydroxyapatite. In some embodiments, the particles of the bone graft composition comprise about 40 wt. % to about 60 wt. % of hydroxyapatite. In some embodiments, the particles of the bone graft composition comprises about 25 wt. % to about 75 wt. % of β-tricalcium phosphate. In some embodiments, the particles of the bone graft composition comprises about 30 wt. % to about 50 wt. % of β-tricalcium phosphate. In some embodiments, the particles of the bone graft composition comprises about 1 wt. % to about 75 wt. % of α-tricalcium phosphate. In some embodiments, the particles of the bone graft composition comprises about 5 wt. % to about 25 wt. % of α-tricalcium phosphate. A summary of these embodiments is shown in Table 6. The endpoints of all ranges are interchangeable, inclusive, and/or combinable.

TABLE 5

| Particle | Wt. % | Size |
|---|---|---|
| Triphasic Particles | 30-70% | 50 μm-2.5 mm |
| Hydroxyapatite | | 50 nm-100 μm |
| Bioactive Glass | 1-30% | 150 μm-300 μm |
| Polyethylene Glycol (PEG) | 30-70% | 1500-2500 grams/mole |
| Glycerol | | NA |

TABLE 6

| Exemplary triphasic particle | Hydroxyapatite (wt. %) | β-tricalcium phosphate (wt. %) | α-tricalcium phosphate (wt. %) |
|---|---|---|---|
| 1 | 25-75% | 25-75% | 1-75% |
| 2 | 40-60% | 30-50% | 5-25% |

In some embodiments, the bone graft composition contains about 30 wt. % to about 70 wt. % of a quadphasic particle comprising hydroxyapatite, β-tricalcium phosphate, α-tricalcium phosphate, and bioactive glass. In some embodiments, the bone graft composition comprises about 30 wt. % to about 70 wt. % of a carrier. Table 7 provides the composition of a preferred embodiment of a bone graft composition comprising quadphasic particles, hydroxyapatite, and a carrier (PEG and glycerol). In some embodiments, the bone graft composition comprises about 25 wt. % to about 75 wt. % of hydroxyapatite. In some embodiments, the bone graft composition comprises about 40 wt. % to about 60 wt. % of hydroxyapatite. In some embodiments, the bone graft composition comprises about 25 wt. % to about 75 wt. % of β-tricalcium phosphate. In some embodiments, the bone graft composition comprises about 30 wt. % to about 50 wt. % of β-tricalcium phosphate. In some embodiments, the bone graft composition comprises about 1 wt. % to about 75 wt. % of α-tricalcium phosphate. In some embodiments, the bone graft composition comprises about 5 wt. % to about 25 wt. % of α-tricalcium phosphate. In some embodiments, the bone graft composition comprises about 1 wt. % to about 30 wt. % of bioactive glass. In some embodiments, the composition comprises about 5 wt. % to about 20 wt. % of bioactive glass. Table 8 summarizes a number of exemplary embodiments of the quadphasic particles of the bone graft composition. The endpoints of all ranges are interchangeable, inclusive, and/or combinable.

TABLE 7

| Particle | Wt. % | Size |
|---|---|---|
| Quadphasic Particles | 40-55% | 50 μm-2.5 mm |
| Hydroxyapatite | | 50 nm-100 μm |
| Polyethylene Glycol (PEG) | 45-60% | 1500-2500 grams/mole |
| Glycerol | | NA |

27

TABLE 8

| Exemplary quadphasic particle of bone graft composition | Hydroxyapatite (wt. %) | β-tricalcium phosphate (wt. %) | α-tricalcium phosphate (wt. %) | Bioactive glass (wt. %) |
|---|---|---|---|---|
| 1 | 25-75% | 25-75% | 1-75% | 1-30% |
| 2 | 40-60% | 30-50% | 5-25% | 5-20% |

Thus, for example, the bone graft composition can comprise about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, about 55 wt %, about 56 wt %, about 57 wt %, about 58 wt %, about 59 wt %, about 60 wt % about 61 wt %; about 62 wt %; about 63 wt %; about 64 wt % about 65 wt %; about 66 wt %; about 67 wt %; about 68 wt %; about 69 wt %; about 70 wt %; about 71 wt %; about 72 wt %; about 73 wt %; about 74 wt %; about 75 wt %; about 76 wt %; about 77 wt %; about 78 wt %; about 79 wt %; or about 80 wt %; of a quadraphasic particle. The bone graft composition can comprise about 40 wt %, about 41 wt %, about 42 wt %, about 43 wt %, about 44 wt %, about 45 wt %, about 46 wt %, about 47 wt %, about 48 wt %, about 49 wt %, about 50 wt %, about 51 wt %, about 52 wt %, about 53 wt %, about 54 wt %, about 55 wt %, about 56 wt %, about 57 wt %, about 58 wt %, about 59 wt %, or about 60 wt % of carrier. The bone graft composition can comprise about 0.5 wt %, about 0.6 wt %, about 0.7 wt %, about 0.8 wt %, about 0.9 wt %, about 1.0 wt %, about 1.1 wt %, about 1.2 wt %, about 1.3 wt %, about 1.4 wt %, about 1.5 wt %, about 1.6 wt %, about 1.7 wt %, about 1.8 wt %, about 1.9 wt %, about 2.0 wt %, about 2.2 wt %, about 2.4 wt %, about 2.6 wt %, about 2.8 wt %, about 3.0 wt %, about 3.2 wt %, about 3.4 wt %, about 3.6 wt %, about 3.8 wt %. about 4.0 wt %, about 4.2 wt %, about 4.6 wt %, about 4.8 wt %; or about 5.0 wt % of hydroxyapatite on the external surface of the bone graft composition.

Bone graft compositions comprising methylcellulose and quadphasic particles can include, for example, about 10 wt % methylcellulose and about 90 wt % quadphasic particles; about 15 wt % methylcellulose and about 85 wt % quadphasic particles; about 20 wt % methylcellulose and about 80 wt % quadphasic particles; about 25 wt % methylcellulose and about 75 wt % quadphasic particles; about 30 wt % methylcellulose and about 70 wt % quadphasic particles; about 35 wt % methylcellulose and about 65 wt % quadphasic particles; about 40 wt % methylcellulose and about 60 wt % quadphasic particles; about 45 wt % methylcellulose and about 55 wt % quadphasic particles; about 50 wt % methylcellulose and about 50 wt % quadphasic particles; or about 55 wt % methylcellulose and about 45 wt % quadphasic particles.

In some embodiments, it is more beneficial to measure components by volume. Measuring components by weight may not be appropriate because the density of synthetic bone graft materials and allografts can substantially vary. For example, when measuring by weight, a material with high density may comprise a high percentage of the overall weight, but represent a very small volume. This can be important when mixing with bone graft materials with carriers (e.g., PEG, glycerol, methylcellulose, water) because carriers are often rapidly absorbed in the body (e.g., within weeks). When using such a composition, there may be only a few dense particles inside the bone void after a few weeks and a relatively large amount of empty space. In some embodiments, the bone graft composition is quadphasic and comprises about 20% v/v to about 60% v/v of a particle comprising hydroxyapatite, β-tricalcium phosphate, α-tricalcium phosphate, and bioactive glass. In some embodiments, the bone graft composition comprises about 40% v/v to about 80% v/v of a carrier. In some embodiments, as summarized in Table 9, the bone graft composition is quadphasic and comprises 10-30% v/v of 300-500 μm particles, 10-30% v/v of 500-1000 μm particles, 0.1-5% v/v of micro-HA particles, 15-45% v/v of glycerol and 15-45% v/v of PEG, wherein the size of the particles is determined by sieving the particles followed by scanning electron microscopy and particle size analysis. The endpoints of all ranges are interchangeable, inclusive, and/or combinable.

TABLE 9

| Component | % v/v |
|---|---|
| Quadphasic particles (300-500 μm) | 10-30% |
| Quadphasic particles (500-1000 μm) | 10-30% |
| Micro-HA particles | 0.1-5% |
| PEG | 15-45% |
| Glycerol | 15-45% |

In some embodiments, the bone graft composition contains: a particle comprising hydroxyapatite, β-tricalcium phosphate, α-tricalcium phosphate, and bioactive glass, wherein the particle has a size in the range of 300 microns to 1 mm; an allograft having a size in a range of about 200 microns to about 1 mm; and a carrier. In some embodiments, the bone graft composition further comprises micro-hydroxyapatite or nano-hydroxyapatite. In some embodiments, there are pores (e.g., submicron pores) within the particles that allow early vascularization. In some embodiments, the carrier comprises a bioresorbable polymer. In some embodiments, the bioresorbable polymer comprises methylcellulose. In some embodiments, the methylcellulose comprises a viscosity weight in a range of about 15 cP to about 4000 cP grams/mole. In some embodiments, the methylcellulose comprises a viscosity weight in a range of about 250 cP to about 1500 cP grams/mole. In some embodiments, the allograft is one or more of the following: demineralized cortical fibers, demineralized cortical bone particles, and demineralized, cancellous bone particles. In some embodiments, the bone graft composition is prepared as a powder.

In some embodiments, the bone graft composition needs to be hydrated at the point of use. In some embodiments, the bone graft composition is hydrated with one or more of fluids from the following list: bone marrow aspirate, platelet-rich plasma, stem cells, blood, BMP-2 or MBMP-7 concentrate, saline, distilled water, or a contrast medium so that the bone graft composition is radiopaque under fluoroscopy. In some embodiments, the bone graft composition is hydrated at a ratio between 1:0.5 to 1:3 bone graft composition to hydration fluid. In some embodiments, the bone graft composition is hydrated at a ratio between 1:1 to 1:2 bone graft composition to hydration fluid.

In some embodiments, the composition comprises about 20 wt. % to about 80 wt. % of the particle comprising hydroxyapatite, β-tricalcium phosphate, α-tricalcium phosphate, and bioactive glass. In such embodiments, the particle has a particle size in a range of about 50 microns to about 2.5 millimeters. In some embodiments, the bone graft composition contains about 3 wt. % to about 30 wt. % of the carrier before hydration. In some embodiments, the bone graft composition contains about 10 wt. % to about 60 wt.

% of allograft. In such embodiments, the allograft has a particle size in a range of about 50 microns to about 2 millimeters. In some embodiments, the bone graft composition exhibits a quadphasic resorption profile.

Methods of Using the Bone Graft Compositions

A bone graft composition according to an embodiment can be used at various target repair sites within a body of a mammal to facilitate bone growth therein. Mammals may include humans, pets such as canines and felines, and domestic animals such as bovines, ovines, equines, porcines, and caprinae.

For example, in some embodiments, the bone graft composition is used at a target repair site in a human patient's spine. The bone graft composition can be inserted in an opening between a transverse process of a first vertebra and a transverse process of a second vertebra. In this manner, the bone graft composition can facilitate growth of a bony bridge between the transverse processes of the first and second vertebrae, such as to achieve posterolateral spinal fusion. In some embodiments, the bone graft composition is deposited in a void or opening between a body of a first vertebra and a body of a second vertebra different than the first vertebra. In this manner, for example, the bone graft composition can facilitate growth of bone between the body of the first vertebra and the body of the second vertebra to achieve interbody fusion of the vertebrae. Bone graft composition may be used for a posterolateral fusion procedure. The graft composition can be radiopaque to visualize the bone graft delivery and the placement on transverse processes and facets.

A bone graft procedure, according to an embodiment, includes a method for implanting a bone graft material or composition (including any bone graft material or composition described herein) at a target repair site within a body of a patient. In some embodiments, the bone graft procedure includes preparing the target repair site of the bone or bony structure within the patient's body to receive the bone graft material. Preparation of the target repair site can include, for example, removing the outer cortex of cortical bone to expose the bleeding cancellous bone with growth factors and stem cells necessary for bone growth. In some procedures, preparation of the target repair site includes re-shaping the site, for example, debriding the site, removing cancerous tissue, for example by removing a portion of the perimeter of the site so that the site has a desired shape. In other procedures, preparation of the target repair site includes decortication to the level of bleeding bone.

In some embodiments, the bone graft composition is shaped for placement at the target repair site. For example, in some embodiments, the user manually manipulates (e.g., squeeze, pinch, stretch, etc.) the bone graft material to form a particular shape.

In some embodiments, the bone graft procedure includes positioning the bone graft material at the target repair site. For example, in some embodiments, the bone graft material is injected into the target repair site. In such embodiments, the bone graft composition is in a flowable state (i.e., it must have a required flowability to transverse the inner chamber of a syringe and be implanted in the target repair site). In some embodiments, the target site includes an implant, such as a 3D-printed cage, port, pores, or aperture on a spinal cage (either monolithic or expandable). In some embodiments, the bone graft composition is used to fill an expandable cage that expands vertically and/or horizontally, or any other direction, once implanted. In some embodiments, the bone graft composition can be applied to other implants, such as hip, knee, nails, facet screws, cortical screws, SI joint fusion implants, other screws, dental implants, cranial implants, etc.

In some embodiments, the bone graft procedure further comprises a step of wetting the bone graft material with a suitable wetting solution, either before or after positioning the bone graft material in the target repair site. In some embodiments, the bone graft material is wetted with a fluid from the patient's body. For example, the blood or platelet rich plasma (PRP), stem cells, BMP-2, and/or BMP-7, etc., from the patient's body can be disposed on the bone graft material or permitted to flow to the bone graft material.

In some embodiments, the bone graft procedure includes mixing the bone graft material with autologous bone, allograft, or a mixture of the two. In some embodiments, the bone graft material is mixed with a pharmaceutical drug for treating pain, inflammation, infection, etc.

In some embodiments, the bone graft composition is in a "ready-to-use" form. In this context, ready-to-use means the bone graft composition is preloaded into a delivery device (e.g., syringe). The bone graft composition does not have to be mixed or reconstituted prior to use. In such embodiments, the user positions the delivery device so that the bone graft composition can flow to the target repair site, and then causes the composition to exit the device to the target site. In some instances, the graft may need to be mixed, rehydrated, or reconstituted prior to use. In such instances, the formulation can depend on what carrier is used with the particles.

In some embodiments, a minimally invasively procedure is desired because such techniques generally decrease the risk of infection and provide a significantly shorter recovery times with less scarring and blood loss. The issue with many autografts, allograft and synthetic bone grafts is the consistency of the material is difficult to be dispensed in a minimally invasive manner. During minimally invasive procedures, a small port in the patient's body is used, which can be impossible to get stiff, gritty, or viscous bone graft through. Bone grafts compositions comprising large particles have a higher chance of clogging when flowing through a small delivery port or into a small crevice. Accordingly, some embodiments herein have an advantage based on improved flowability and reduced particle size.

In some embodiments, the synthetic bone graft composition demonstrates a low increase in extrusion force as it is pushed through small openings. This trait is important in orthopedic procedures and, in particular, minimally invasive spine procedures because it allows the graft to flow down small cannulas into difficult orthopedic implants such as 3D printed cages, facet screws, pedicle screws, SI fusion implants, and expandable cages having small entry ports. Such implants help hold the spine in place as it heals. In particular, an expandable cage can be inserted into the body through small incisions or portals, and then expand to its full size while in the body. An expandable implant requires relatively small incisions and can increase its size (height and/or width) can be adjusted to better fit the patient's anatomy. In some embodiments, where bone growth is intended, filling the implant fully with bone graft provides an improved chance for bone growth and integration. Maximizing vertebra endplate contact improves chances of fusion. In some embodiments, the bone graft material is easily dispensed within 3D printed implants for hips, knees, fracture plates, spine cages, screws, expandable cages, pedicle screws, cranial mesh, facet screws, plates, anchors, SI fusion implants, dental implants, etc.

Figure 16A:
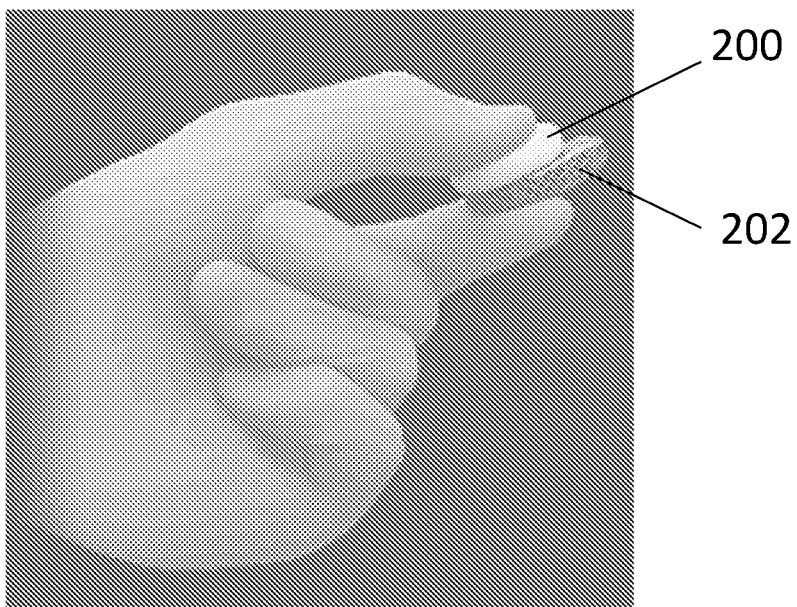
FIG. 16A is a depiction of a 3D printed structure and a bone graft composition prior to entering the structure, in accordance with embodiments disclosed herein.
Figure 16B:
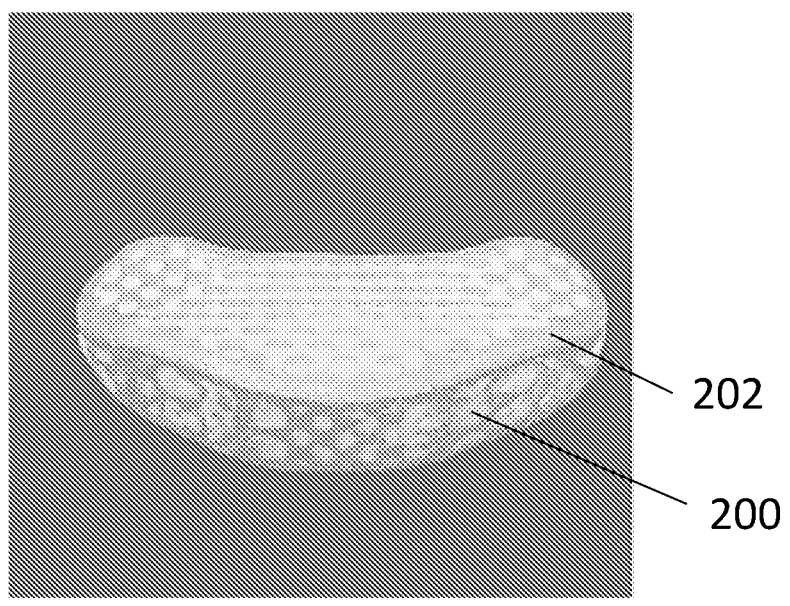
FIG. 16B is a depiction of the 3D printed structure and bone graft composition of FIG. 16A, after the composition has entered the structure, in accordance with embodiments disclosed herein.

The use of 3D printing technology allows for the creation of complex and/or custom implants. For example, implants can include pores (e.g., micro- or nano-pores) or other intricate scaffolding designs that permit the flowable bone graft to enter and fill the cage. FIGS. 16A and 16B provide one such example. FIG. 16A shows a bone graft composition (200) about to be pressed into a 3D printed cage (202). The improved flowability of the composition (200) allows it to easily enter and fill the cage (202), as shown in FIG. 16B.

Bone Graft Composition Kits

In various embodiments, a kit for bone graft procedures is provided. In some embodiments, the bone graft composition can be prepared for the bone graft material kit. For example, the bone graft material kit can include the bone graft composition and a delivery device for administering the composition to the patient. In some embodiments, the kit includes an additional implant device, such as a 3D printed cage or loading case/retainer for implant in which graft can be injected into the case to fill the implant. In such embodiments, the loading case is intended to enclose the cage to allow the graft to pressurize and fill the porous cage or implant. The retainer can be configured to connect to a syringe or graft delivery system/device to force the graft in.

In some embodiments, the bone graft composition is supplied as an implant or a prefilled cartridge preloaded into an open bore syringe or elongate tube. In some embodiments, the bone graft material kit includes a bone graft syringe assembly for delivering the bone graft material. In such embodiments, the bone graft syringe assembly comprises: a syringe barrel having a proximal end, a distal end, and an inner chamber adapted for receiving the bone graft composition, the inner chamber having a proximal opening and a distal opening (e.g., an elongate tube); and, a plunger adapted to expel the bone graft material through the distal opening of the inner chamber, with the plunger slidably received within the inner chamber through the proximal opening. In such embodiments, the plunger may be advanced within the tube to expel bone graft by means of a ratcheting, worm gear, cable, or use other means to advance the plunger. The plunger can also be advanced via a push rod. In such embodiments, the force needed to expel the bone graft composition from the tube can be generated manually, mechanically, electrically, via battery, pneumatically, or any other suitable mechanism. In some embodiments, the surface of the plunger is smooth. In some embodiments, the surface of the plunger contains teeth, rings, notches, or other features for gripping the plunger and preventing migration. Further, a pawl or other internal fixture may be used to advance the plunger. In some embodiments, the handle may include a trigger to squeeze, a knob to rotate, or a mallet. In some embodiments, the bone graft composition is pre-filled in the elongated tubes and attached to a delivery apparatus for advancing the bone graft out of the tube and into the delivery site. In such embodiments, the pre-filled tube with bone graft may also be used with a push rod to avoid the cost of using a delivery apparatus. In some embodiments, the end of the tube is adapted with an array of tips designed to reach narrow disc spaces, post fill cages, or hard to reach targets. See, e.g., U.S. Pat. No. 10,238,507, the content of which is hereby incorporated by reference in its entirety. Although specific components of U.S. Pat. No. 10,238,507 are discussed above, the entire content of U.S. Pat. No. 10,238,507 is hereby incorporated by reference.

In some embodiments, the bone graft delivery device includes a trigger or knob that is actuated to deliver bone graft material through a tube and distal tip to a desired surgical location. In some embodiments, the device includes a plunger with notches or teeth that is simultaneously pushed distally by a pawl or gear to help deliver bone graft material through the tube. In some embodiments, the trigger or other actuation mechanism is configured to deliver a controlled release amount of bone graft material during actuation of the device (e.g., 0.5 cc of bone graft material per complete squeeze of the trigger). The trigger or other actuation mechanism may be operated manually, mechanically, battery powered, electric, pneumatic, or any other means of generating force. The pre-filled tube can contain the bone graft composition and attached to the delivery apparatus to save time in the operating room and to prevent cross contamination in a sterile field. The prefilled tube may by packaged in the same sterile package as the delivery device or in a separate sterile package.

In some embodiments, the bone graft composition is loaded into the elongate tube using a loading device. The loading device may have a threaded spindle drive, straight plunger, ratchet, or another mechanism configured to force the bone graft composition into the elongate tube. The force applied may be manual, mechanical, electric, hydraulic, or another system for generating and supplying force. The tube can be any suitable volume. In some embodiments, for example, the tube ranges from 1 cubic centimeter (cc) to 10 cc. The tube can be any suitable size. For example, in some embodiments, the outer tube diameter is from 2 mm to 12 mm. In some embodiments, the diameter is important for graft flowability and for accessing bone voids or disc spaces. In some embodiments, the tube has a cylindrical, square, or any other suitable cross-sectional shape. In some embodiments, the kit includes a plurality of tubes.

In some embodiments, the bone graft composition has the required flowability for traveling through the inner chamber of the syringe and be implanted in the target area of the patient. In some embodiments, if the bone graft composition is overly viscous, then it may not be sufficiently expelled from the syringe. As disclosed herein, the bone graft composition has improved flowability relative to alternative compositions.

In some embodiments, the syringe barrel of the kit includes end caps on each end of the tube. In some embodiments, the syringe barrel further comprises an O-ring or gasket for maintaining an air-tight seal between the cap and tube. In such embodiments, the O-ring or gasket can be made of silicon or any other material suitable for maintaining an air-tight seal between the cap and the tube. In some embodiments, the sealing cap may be threaded onto the tube. Alternatively, the cap may be plugged into the tube, snapped onto the tube, or any other suitable way of engaging the cap and tube. In some embodiments, the tube contains markings (e.g., indicating volume). In some embodiments, the tube includes a radiopaque marker at or near the distal end that allows the user to observe the tube through imaging during surgery. In some embodiments, the tube is flexible (e.g., bendable). In some embodiments, the tube is rigid.

In some embodiments, the tube is sterilized using any suitable sterilization method. For example, the sterilization method can be electron-beam, ethylene oxide, steam, gamma radiation, or another suitable method of sterilization. Once sterilized, the tube is placed in a single pouch or double pouch and then sealed, providing a single or double sterile barrier. In some embodiments, additional packaging is utilized. For example, Tyvek, foil pouch, HDPE, LDPE, or other means to keep bone graft sterile and protected can be utilized. Other packaging is also contemplated.

In some embodiments, the tube comprises one or more of an array of polymers, including but not limited to, polypropylene, polycarbonate, polysulfone, etc. In some embodiments, the tube is made out of metal or metal alloy, including, e.g., stainless steel.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Bone Growth Study

INVENTIVE EXAMPLE 1 (EX1) is a composition comprising a quadphasic particles comprising hydroxyapatite, about 30 wt. % to about 50 wt. % of β-tricalcium phosphate, 5 wt. % to about 25 wt. % of α-tricalcium phosphate, about 5 wt. % to about 20 wt. % of bioactive glass. The quadphasic particles make up about 30 wt. % to about 70% wt. % of the composition with the quadphasic particles having a particle size in the range of about 250 μm to about 1000 μm. The composition also comprising about 0.01 wt. % to about 10 wt. % Hydroxyapatite particles with the hydroxyapatite particles having a particle size in the range of about 50 nm to about 100 μm. The composition also comprises a polyethylene glycol (PEG) and glycerol carrier which makes up about 40 wt. % to about 65 wt. % of the composition. The PEG comprising a molecular weight in a range of about 1500 grams/mole to about 2500 grams/mole. This preferred embodiment of a quadphasic bone graft composition demonstrated adequate control with respect to application of the bone graft material (viscosity and flowability) and the most promising results with respect to the growth and restoration of bone following application.

INVENTIVE EXAMPLE 2 (EX2) is a composition comprising a triphasic particle comprising hydroxyapatite, about 30 wt. % to about 50 wt. % of β-tricalcium phosphate, 5 wt. % to about 25 wt. % of α-tricalcium phosphate, and the remainder being a carrier. The triphasic particles make up about 30 wt. % to about 70% wt. % of the composition with the triphasic particles having a particle size in the range of about 250 μm to about 1000 μm. The composition also comprises about 0.01 wt. % to about 10 wt. % hydroxyapatite particles with the hydroxyapatite particles having a particle size in the range of about 50 nm to about 100 μm. The composition also comprises a polyethylene glycol (PEG) and glycerol carrier which makes up about 40 wt. % to about 65 wt. % of the composition. The PEG comprising a molecular weight in a range of about 1500 grams/mole to about 2500 grams/mole. This preferred embodiment of a triphasic bone graft composition demonstrated adequate control with respect to application of the bone graft material (viscosity and flowability) and the most promising results with respect to the growth and restoration of bone following application.

COMPARATIVE EXAMPLE 1 (CE1) is NovaBone Bioactive Synthetic Bone Graft Putty, a commercially-available synthetic bone graft putty comprising bioactive glass.

The purpose of the experiment was to evaluate and compare the two Inventive Example compositions with the Comparative Example and a control using a critical sized bone defect study model. A total of 55 rabbits underwent surgery to create unicortical 6 mm diameter×approximately 8-10 mm deep defects in each distal femoral condyle. The surgically created bone defects received either the Inventive Example 1 composition, Inventive Example 2 composition, Comparative Example 1 composition, or an empty control. All experiments were conducted in a laboratory that is certified for good manufacturing practices. Bone growth and residual composition were monitored by Computed Tomography (CT scan) imaging in order to compare the resorption and bone growth differences between the compositions. Imaging was acquired for each of the subjects at 4 weeks, 8 weeks, and 12 weeks after the procedure ("Post-op"). The CT scan images are shown in FIGS. 1-12. The data from the CT scan imaging has been quantified and the results are provided in Table 10.

TABLE 10

| Time Point | Treatment | Calculation | HISTOMORPHOMETRY (QUANTITATIVE) | | | | |
|---|---|---|---|---|---|---|---|
| | | | Total Region of Interest (ROI) Area (mm$^2$) | Residual Implant Area (mm$^2$) | Residual Implant Area (% of Total ROI) | Bone Area (mm$^2$) | Bone Area (% of Total ROI) |
| 0 Day | EXAMPLE 1 (EX1) | n | 6 | 6 | 6 | 6 | 6 |
| | | Mean | 67.998 | 42.929 | 63.6% | 1.452 | 2.1% |
| | | Std Dev | 6.541 | 4.108 | 8.0% | 0.672 | 1.0% |
| | EXAMPLE 2 (EX2) | n | 6 | 6 | 6 | 6 | 6 |
| | | Mean | 60.712 | 13.332 | 22.4% | 2.082 | 3.2% |
| | | Std Dev | 9.911 | 12.405 | 20.3% | 1.688 | 2.4% |
| 4 Week | EXAMPLE 1 (EX1) | n | 7 | 7 | 7 | 7 | 7 |
| | | Mean | 53.762 | 14.561 | 27.1% | 14.722 | 27.5% |
| | | Std Dev | 7.763 | 3.822 | 6.1% | 2.644 | 4.1% |
| | EXAMPLE 2 (EX2) | n | 7 | 7 | 7 | 7 | 7 |
| | | Mean | 52.741 | 22.241 | 41.7% | 9.725 | 18.5% |
| | | Std Dev | 7.687 | 6.547 | 7.6% | 1.965 | 2.9% |
| | COMPARATIVE EXAMPLE 1 (CE1) | n | 7 | 7 | 7 | 7 | 7 |
| | | Mean | 64.084 | 25.569 | 40.0% | 8.379 | 12.9% |
| | | Std Dev | 11.882 | 10.512 | 14.2% | 3.324 | 4.5% |
| | Defect Left Empty (Negative Control) (NC) | n | 7 | 0 | 0 | 7 | 7 |
| | | Mean | 48.379 | NA | NA | 5.046 | 10.7% |
| | | Std Dev | 6.984 | NA | NA | 1.182 | 3.3% |

TABLE 10-continued

| | | | HISTOMORPHOMETRY (QUANTITATIVE) | | | | |
|---|---|---|---|---|---|---|---|
| Time Point | Treatment | Calculation | Total Region of Interest (ROI) Area (mm$^2$) | Residual Implant Area (mm$^2$) | Residual Implant Area (% of Total ROI) | Bone Area (mm$^2$) | Bone Area (% of Total ROI) |
| 8 Week | EXAMPLE 1 | n | 7 | 7 | 7 | 7 | 7 |
| | (EX1) | Mean | 47.496 | 13.442 | 28.0% | 12.367 | 26.1% |
| | | Std Dev | 8.443 | 4.444 | 6.3% | 2.510 | 2.6% |
| | EXAMPLE 2 | n | 7 | 7 | 7 | 7 | 7 |
| | (EX2) | Mean | 52.098 | 23.369 | 44.9% | 11.924 | 22.8% |
| | | Std Dev | 3.690 | 2.440 | 3.4% | 2.189 | 3.4% |
| | COMPARATIVE | n | 7 | 7 | 7 | 7 | 7 |
| | EXAMPLE 1 (CE1) | Mean | 62.918 | 11.917 | 18.7% | 16.713 | 26.3% |
| | | Std Dev | 11.356 | 4.256 | 4.6% | 4.899 | 4.8% |
| | Defect Left | n | 7 | 0 | 0 | 7 | 7 |
| | Empty (Negative | Mean | 33.432 | NA | NA | 1.599 | 4.6% |
| | Control) (NC) | Std Dev | 12.251 | NA | NA | 1.229 | 2.6% |
| 12 Week | EXAMPLE 1 (EX1) | n | 7 | 7 | 7 | 7 | 7 |
| | | Mean | 61.694 | 11.853 | 19.3% | 17.289 | 27.9% |
| | | Std Dev | 8.730 | 3.872 | 6.8% | 3.927 | 4.4% |
| | EXAMPLE 2 (EX2) | n | 7 | 7 | 7 | 7 | 7 |
| | | Mean | 52.078 | 20.810 | 39.9% | 13.243 | 26.2% |
| | | Std Dev | 6.510 | 3.421 | 4.7% | 4.119 | 10.5% |
| | COMPARATIVE | n | 7 | 7 | 7 | 7 | 7 |
| | EXAMPLE 1 (CE1) | Mean | 57.720 | 7.242 | 12.4% | 14.596 | 25.4% |
| | | Std Dev | 9.086 | 3.119 | 4.5% | 3.740 | 5.6% |
| | Defect Left | n | 7 | 0 | 0 | 7 | 7 |
| | Empty (Negative | Mean | 37.167 | NA | NA | 1.726 | 4.9% |
| | Control) (NC) | Std Dev | 6.399 | NA | NA | 1.269 | 4.3% |

In Table 10, the last column indicates the percent of bone growth in the region of interest for each subject over time, and the third data column indicates the percent of residual implant remaining for each subject over time. As the components in a bone graft compositions are absorbed in a target site, it would be expected to see the percent of bone growth to increase while the percent of residual implant decreases. Applicants have developed compositions that unexpectedly provide a substantial increase in bone growth over the first 4 weeks while also maintaining a substantial amount of residual implant after 12 weeks. As explained in more detail below, EX1 and EX2 provide excellent initial bone growth while maintaining a substantial amount of implant after 12 weeks for continued bone growth.

Figure 2:
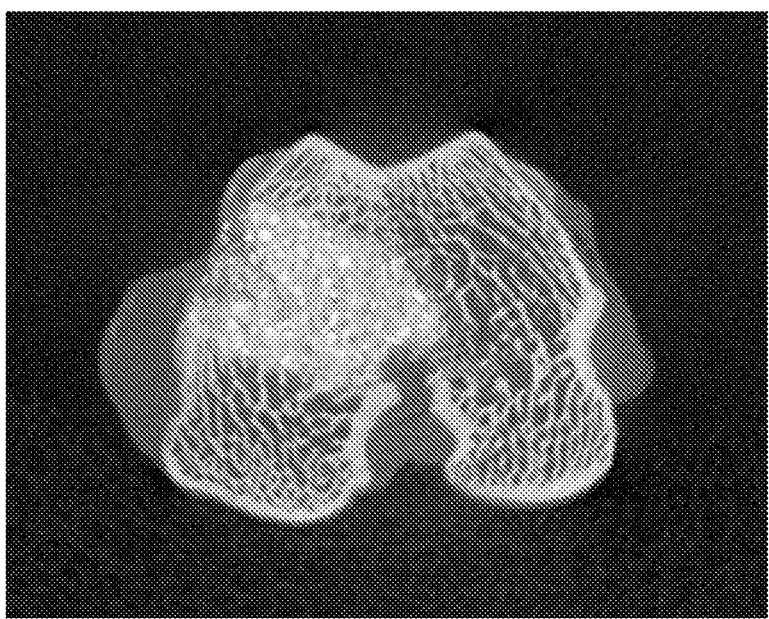
FIG. 2 is a CT image of a rabbit hip treated with Example 1, four (4) weeks after surgery, in accordance with embodiments disclosed herein.
Figure 3:
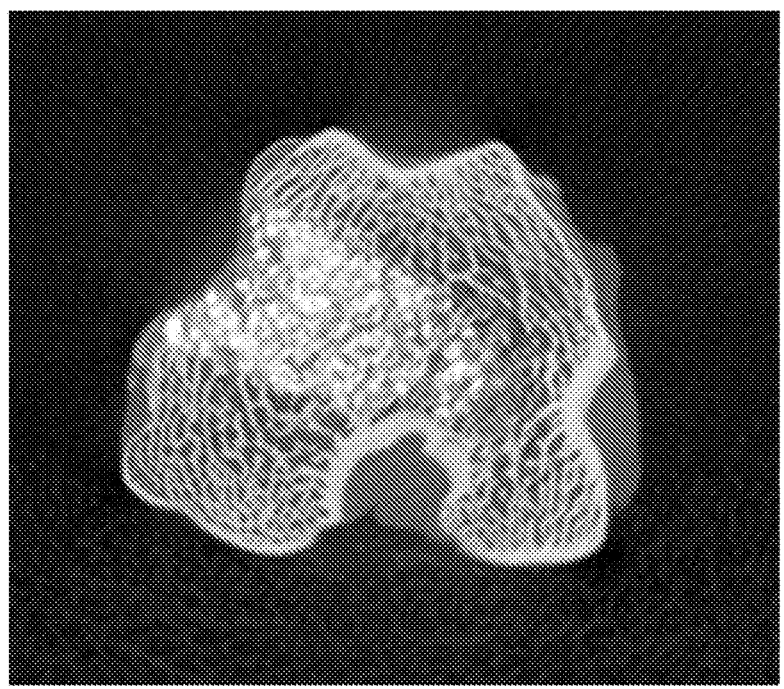
FIG. 3 is a CT scan image of a rabbit hip treated with Example 2, four (4) weeks after surgery, in accordance with embodiments disclosed herein.
Figure 4:
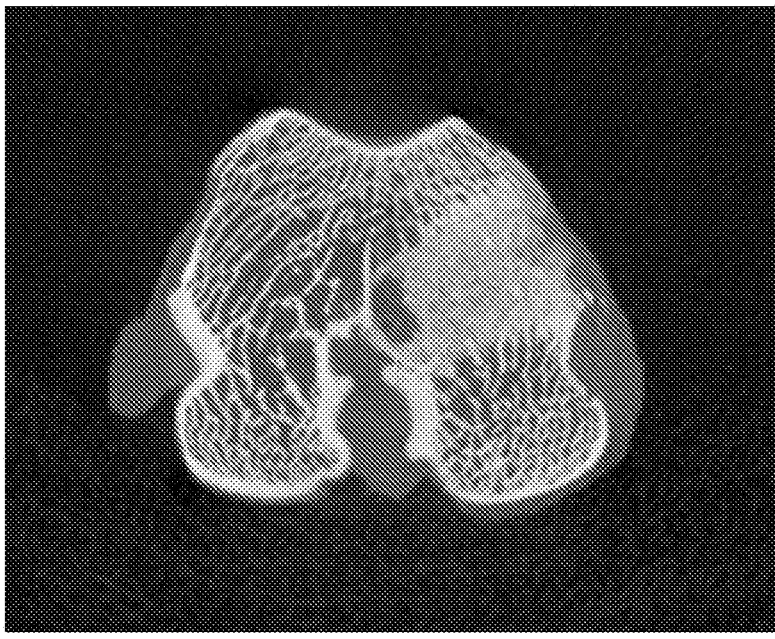
FIG. 4 is a CT scan image of a rabbit hip treated with Comparative Example 1, four (4) weeks after surgery.

After 4 weeks, the percent of bone growth increased to 27.5% in EX1 and 18.5% in EX2, and the percent of residual implant is 27.1% and 41.7%, respectively. By contrast, the percent of bone growth increased only to 12.9% in CE1 and 10.7% in NC, and the percent of residual implant is 40.0% in CE1. The CT scans for this data are shown in FIGS. 1-4. Specifically, FIG. 1 shows the area in the NC subject where the drill void was created and the void remains generally empty (i.e., minimum bone growth). By contrast, FIGS. 2-4 show the drill void filled with bone graft and bone. In FIG. 2, the void is filled with quadphasic bone graft (EX1) and bone (collectively, the white material). There are no cracks, gaps, or areas of black space in the filled void that would indicate resorption of the bone graft. In FIG. 3, the drill void is filled with triphasic bone graft (EX2) and bone (collectively, the white material), and there are no cracks, gaps, or areas of black space. FIG. 4 shows the drill void filled with CE1.

Figure 5:
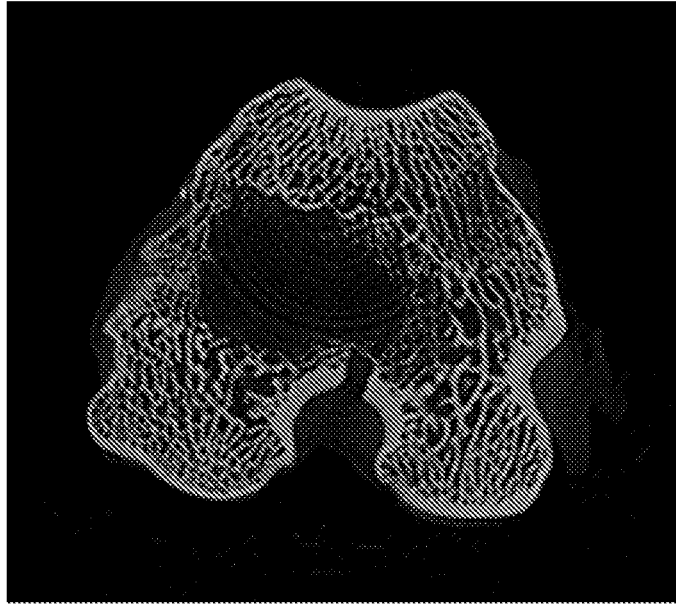
FIG. 5 is a CT scan image of the Negative Control rabbit hip, eight (8) weeks after surgery.
Figure 6:
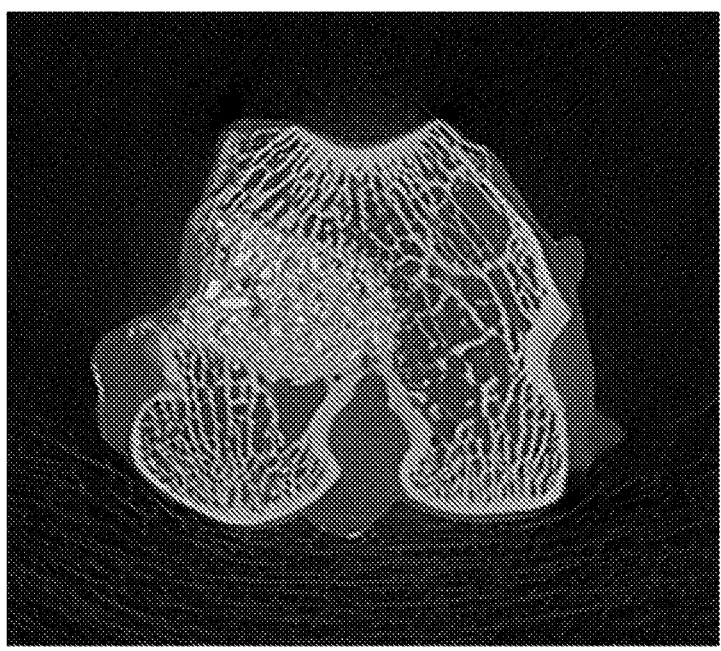
FIG. 6 is a CT scan image of a rabbit hip treated with Example 1, eight (8) weeks after surgery, in accordance with embodiments disclosed herein.
Figure 7:
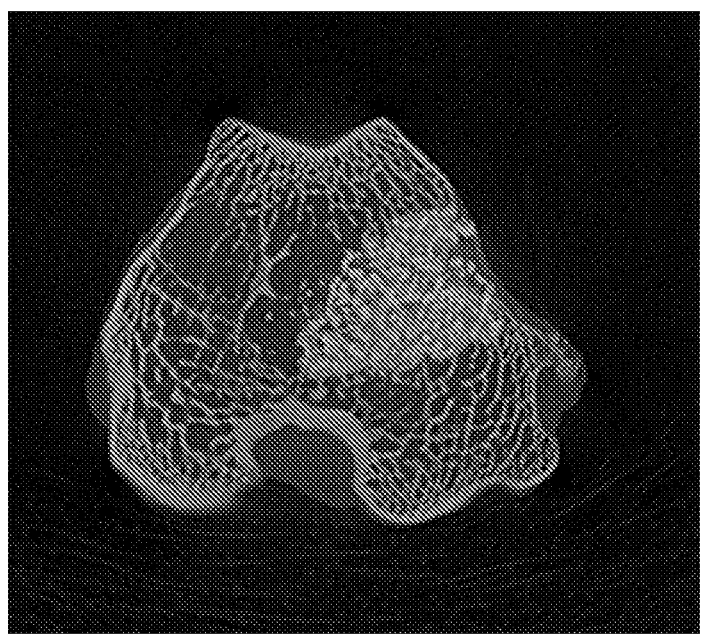
FIG. 7 is a CT scan image of a rabbit hip treated with Example 2, eight (8) after surgery, in accordance with embodiments disclosed herein.
Figure 8:
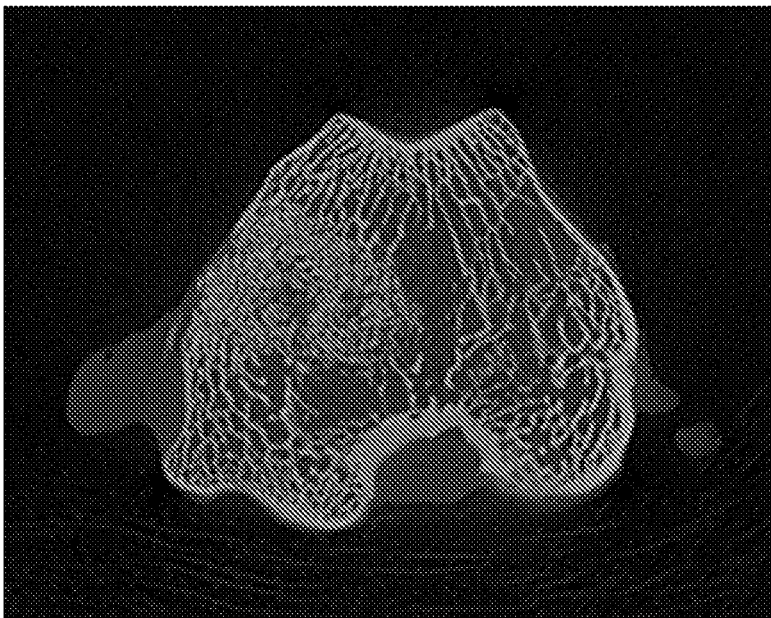
FIG. 8 is a CT scan image of a rabbit hip treated with Comparative Example 1, eight (8) weeks after surgery.

After 8 weeks, the percent of bone growth increased to 26.1% for EX1, 22.8% for EX2, and 26.3% for the CE1; and the percent of residual implant is 28.0%, 44.9%, and 18.7%, respectively. The results are shown in FIGS. 5-8. The negative control in FIG. 5 shows the drill void remaining essentially empty with only 4.6% bone growth. FIG. 6 shows the drill void filled with quadphasic bone graft (EX1) and bone (collectively, the white material), with no cracks, gaps, or areas of black space. FIG. 7 shows the drill void filled with triphasic bone graft (EX2) and bone (collectively, the white material), and there are no cracks, gaps, or areas of black space. FIG. 8 shows the drill void filled with white material (CE1 and bone), and there are some areas in black indicating resorption.

Figure 9:
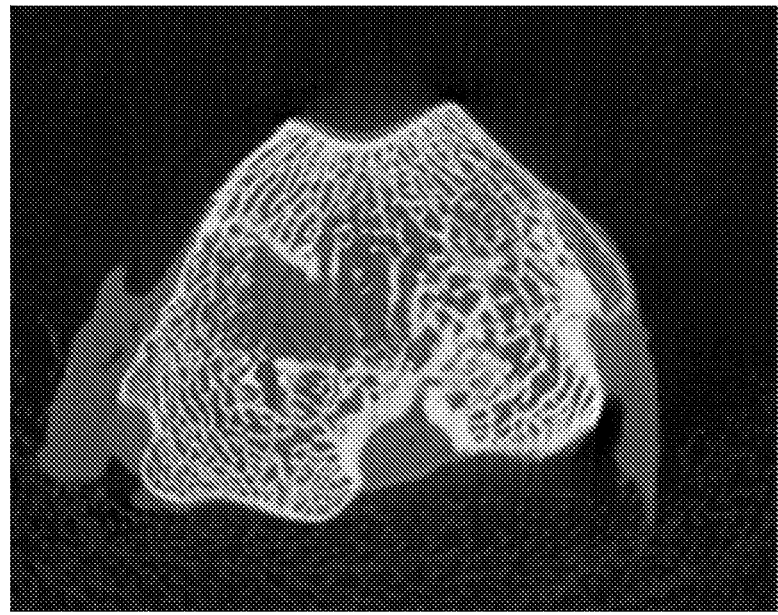
FIG. 9 is a CT scan image of the Negative Control rabbit hip, twelve (12) weeks after surgery.
Figure 10:
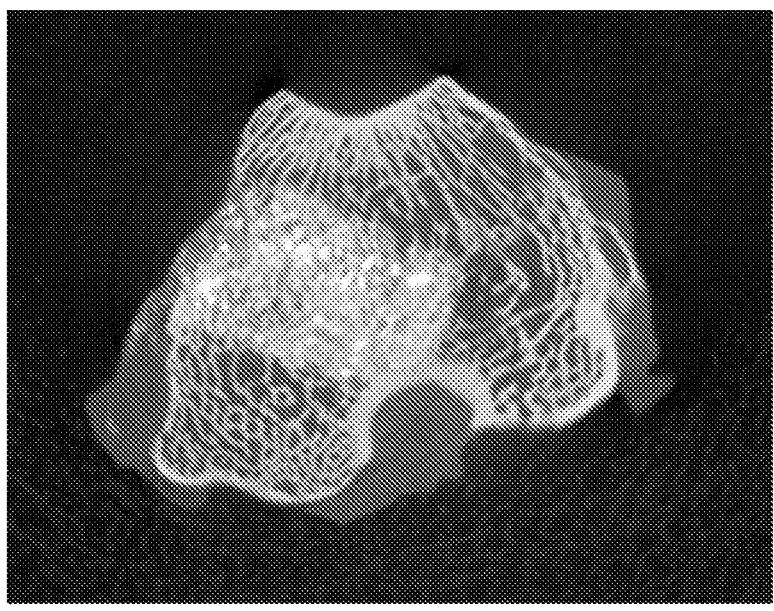
FIG. 10 is a CT scan image of a rabbit hip treated with Example 1, twelve (12) weeks after surgery, in accordance with embodiments disclosed herein.
Figure 11:
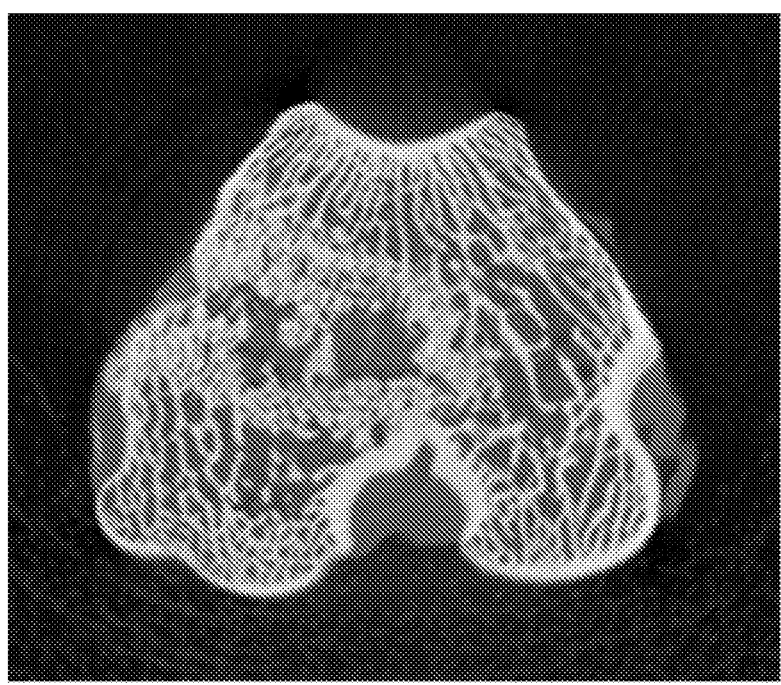
FIG. 11 is a CT scan image of a rabbit hip treated with Comparative Example 1, twelve (12) weeks after surgery.
Figure 12:
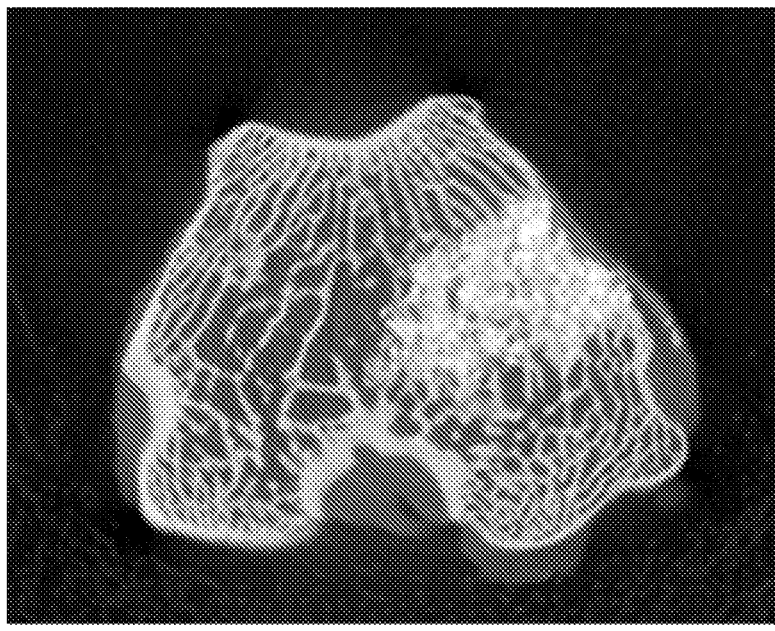
FIG. 12 is a CT scan image of a rabbit hip treated with Example 2, twelve (12) weeks after surgery, in accordance with embodiments disclosed herein.

After 12 weeks, the percent of bone growth increased to 27.9% for EX1, 26.2% for EX2, and 25.4% for CE1; and the percent of residual implant is 19.3%, 39.9%, and 12.4%, respectively. The results are shown in FIGS. 9-12. The negative control in FIG. 9 shows the drill void remaining mostly empty, with only 4.9% bone growth. FIG. 10 shows the drill void filled with quadphasic bone graft (EX1) and bone (collectively, the white material). There are no cracks, gaps, or areas of black space indicating resorption. FIG. 11 shows the drill void treated with the CE1. In FIG. 12, the void is filled with white material (bioactive glass and bone). There is a significant amount of black area indicating resorption. FIG. 12 shows the drill void filled with triphasic bone graft (EX2) and bone (collectively, the white material), with no cracks, gaps, or areas of black space.

Figure 13:
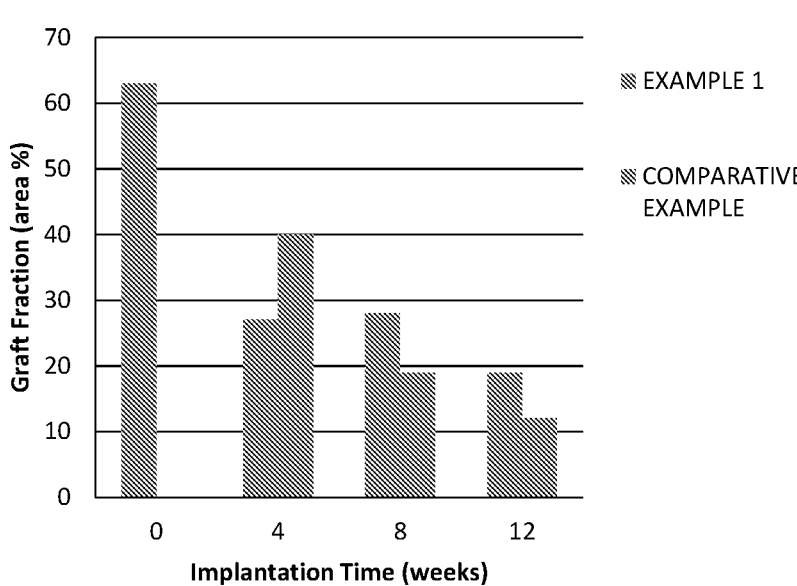
FIG. 13 is a graph showing the percent of residual graft remaining over time for an Example and Comparative Example described herein.
Figure 14:
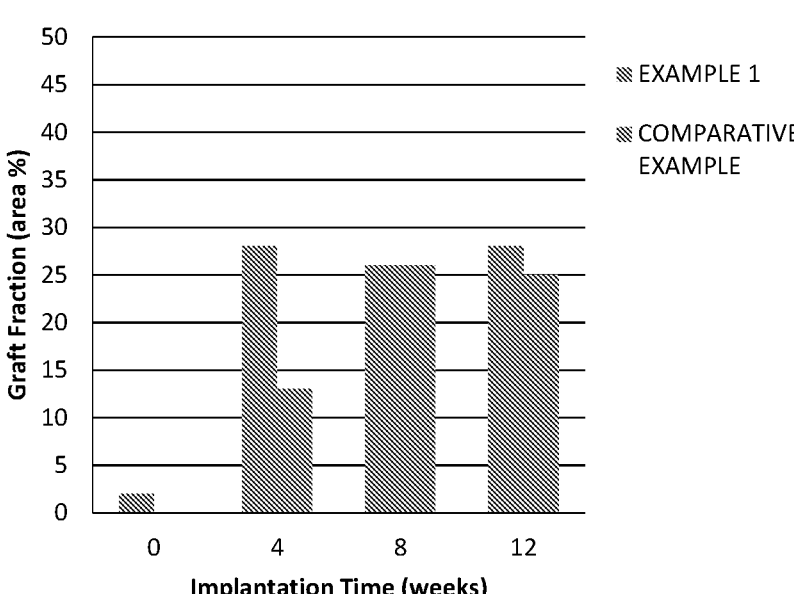
FIG. 14 is a graph showing the percent of new bone growth over time for an Example and Comparative Example described herein.

Inventive Examples EX1 and EX2 exhibited a substantially faster initial bone growth. The percent of bone growth data in Table 10 is summarized in FIG. 14. In addition to the improved rates of bone growth observed for EX1 and EX2, there is also a significant amount of residual composition remaining in the filled void after 12 weeks. The increased percentage of residual bone graft composition should lead to further bone growth and healing. Without being bound by any particular scientific theory, it is believed that the improved percent of residual implant is due to the triphasic and quadphasic nature of EX1 and EX2, respectively. The percent of residual composition data from Table 1 is summarized in FIG. 13.

Example 2

Flowability Study

Additional benefits have been observed for the inventive bone graft compositions relative to known bone graft compositions. Flowability relates to the ability of the substance to flow through a syringe or elongated tube. For instance, known compositions are typically very viscous and have inadequate flowability when administered through a syringe or elongate tube. By contrast, the inventive bone graft compositions have significantly improved flowability. Without being bound by any particular scientific theory, it is believed that the improved flowability is due to the relatively small size of the particles and the carrier formulation. This flowability is increasingly important when the graft is being pushed through small openings or into intricate crevices of a spinal cage, screw, implant pore, or implant port.

Figure 15:
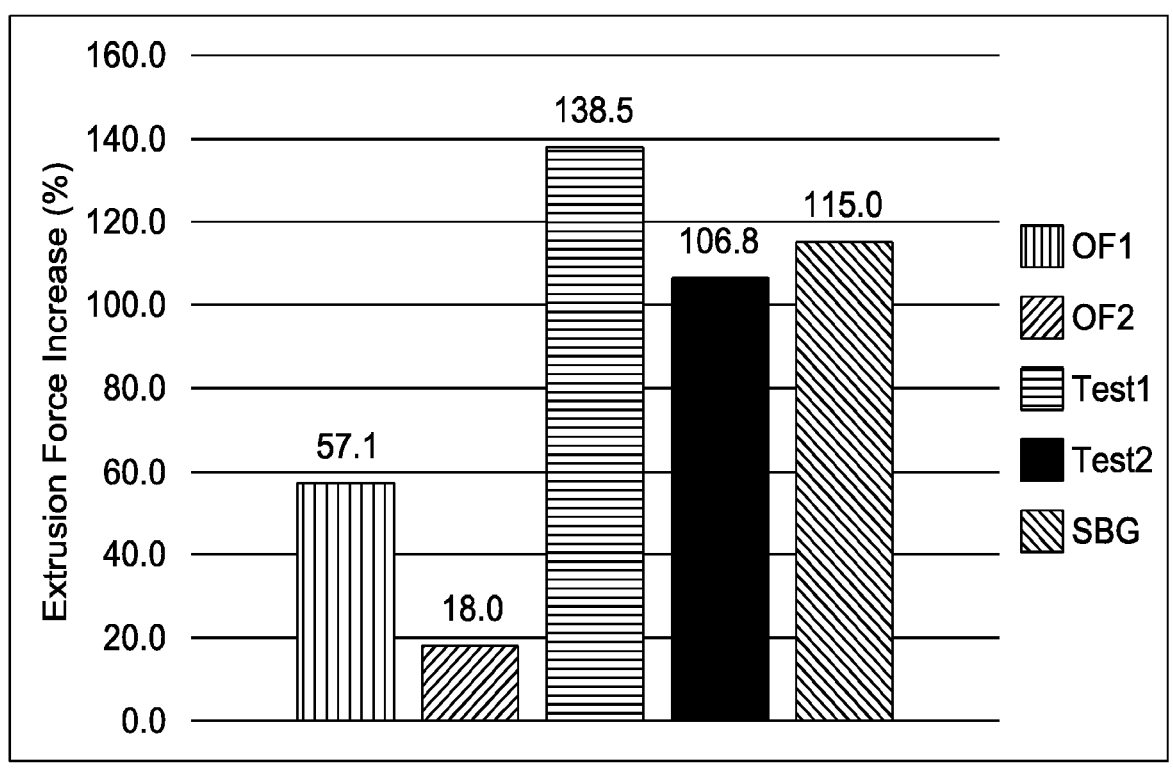
FIG. 15 is a graphical representation showing the improved flowability for the disclosed bone graft compositions, in accordance with embodiments disclosed herein.

FIG. 15 is a graphical representation showing the improved flowability for the inventive compositions. In particular, FIG. 15 shows an increase in the minimum extrusion force required to push various synthetic bone graft compositions through a 3.0 mm orifice compared to a 6.0 mm orifice. For example, if a minimum of 5 lbf is required to push a synthetic bone graft formulation through a 6.0 mm orifice and 10 lbf is required to push the same synthetic bone graft formulation through a 3.0 mm orifice, the increase in extrusion force would be 100%, per the following Formula III:

$$Force\ Increase = \frac{F_{6\,mm} - F_{3\,mm}}{F_{3\,mm}} \times 100\%$$

Formula III

INVENTIVE EXAMPLE 3 (EX3) is a composition comprising about 40-60 wt. % quadphasic particles and about 40-60 wt. % carrier. The particles comprise about 40-60% hydroxyapatite, about 30-50 wt. % of β-tricalcium phosphate, 5-25 wt. % of α-tricalcium phosphate, about 5-20 wt. % of bioactive glass, and the remainder being a carrier containing polyethylene glycol (PEG) with an average molecular weight of up 2000 and glycerol. The carrier comprises 35-50 wt. % glycerol and 50-65 wt. % PEG. The composition includes particles having maximum particle sizes of 1.0 mm or less as determined by breaking down and sieving out the particles, followed by scanning electron microscopy and particle size analysis.

INVENTIVE EXAMPLE 4 (EX4) is a composition comprising about 40-60 wt. % quadphasic particles and about 40-60 wt. % carrier. The particles comprise about 40-60% hydroxyapatite, about 30-50 wt. % of β-tricalcium phosphate, 5-25 wt. % of α-tricalcium phosphate, about 5-20 wt. % of bioactive glass, and the remainder being a carrier consisting of polyethylene glycol (PEG) with an average molecular weight of 2000 and glycerol. The carrier comprising 40-60 wt. % glycerol and 40-60 wt. % PEG. The composition includes particles having maximum particle sizes of 1.0 mm or less as determined by breaking down and sieving out the particles, followed by scanning electron microscopy and particle size analysis.

COMPARATIVE EXAMPLE 2 (CE2) and COMPARATIVE EXAMPLE 3 are synthetic bone graft compositions comprising about 40-60 wt. % quadphasic particles and 40-60 wt. % carrier. The particles comprising about 40-60% hydroxyapatite, about 30-50 wt. % of β-tricalcium phosphate, about 5-25 wt. % of α-tricalcium phosphate, and about 5-20 wt. % of bioactive glass. CE2 includes carrier with glycerol and a polyethylene glycol (PEG) having an average molecular weight of up to 10,000. The carrier comprises 35-50 wt. % glycerol and 50-65 wt. % PEG. The particles in the compositions of CE2 have particle sizes of up to 2.0 mm. CE3 includes carrier with glycerol and a polyethylene glycol (PEG) having an average molecular weight of up to 2,000. The carrier comprising 20-40 wt. % glycerol and 60-80 wt. % PEG. The particles in the compositions of CE2 have particle sizes of up to 2.0 mm. CE2 is the same formulation as EX3 except for the presence of larger particle sizes and higher molecular weight PEG carrier. CE3 is the same formulation as EX4 except for the presence of larger particle sizes and the higher percentage of PEG to glycerol.

COMPARATIVE EXAMPLE 4 (CE4) is NovaBone Bioactive Synthetic Bone Graft Putty a commercially available synthetic bone graft composition. This product has the reputation of having great handling characteristics. It is believe their composition comprises about 60-80 wt. % particles and 20-40 wt. % carrier. The particles comprise 100 wt. % bioactive glass. CE4 includes a carrier with glycerol and a polyethylene glycol (PEG). The particles in the composition of CE4 have particle sizes of up to about 300 μm.

Inventive synthetic bone graft compositions EX3 and EX4 were tested and compared to CE2, CE3, and CE4. As shown in FIG. 15, EX3 (OF1) and EX4 (OF2) exhibited an extrusion force increase of 57% and 18%, respectively as determined using Formula III; and, CE2 (Test 1), CE3 (Test 2), and CE4 (synthetic bone graft; SBG) each exhibited an extrusion force increase of over 100% (139%, 107%, and 115%, respectively) as determined using Formula III. Accordingly, the comparative data shows the extrusion force increase for the Inventive synthetic bone graft compositions in EX3 and EX4 was significantly less than that for CE2, CE3, and CE4.

Without being bound to a particular scientific theory, one reason for the significant difference in extrusion force increase is due to the particle size of the synthetic bone graft formulations. EX3 (OF1) and EX4 (OF2) have maximum particle sizes of 1.0 mm or less, whereas CE2 (Test 1) and CE3 (Test 2) have larger minimum particle sizes of up to 2.0 mm. Another reason for the significant difference in extrusion force increase is due to the carrier. CE2 (Test 1) utilizes a polyethylene glycol (PEG) carrier with an average molecular weight of up to 10,000. That molecular weight is much higher than the carrier used in EX3 and EX4, and such an increase in weight increases the density and the melting point of the carrier, which in turn causes the composition to become hard and more solid at room temperature. As a result, higher shear forces are required to extrude CE2 and CE3 through an orifice, and a larger increase in the minimum extrusion force was observed. Though CE4 comprised of particles with smaller particle sizes than EX3 and EX4, CE4 comprised entirely of bioactive glass and carrier, thus suggesting that the particle composition or makeup of the bone graft composition has a significant effect on the observed extrusion force.

Compared to the EX3 and EX4, the CE3 carrier had a higher ratio of PEG to glycerol. At room temperature, glycerol is a liquid and 2000 PEG is a semisolid. The PEG used in CE3 has the same average molecular weight (2000) as the PEG used in EX3 and EX4. The relative increase in volume of PEG and decrease in volume of glycerol resulted in similar effects as the bone graft formulation used in CE2. For example, the graft was harder and more solid at room temperature. Accordingly, higher shear forces were required to extrude CE2 through an orifice, resulting in the larger increase in minimum extrusion force required.

The foregoing is provided for purposes of illustrating, explaining, and describing embodiments of this application. Modifications and adaptations to these embodiments will be apparent to those skilled in the art and may be made without departing from the scope or spirit of this application. All such modifications are intended to be encompassed within the below claims.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

We claim:

1. A sintered particle comprising one or more particles each of hydroxyapatite, β-tricalcium phosphate, α-tricalcium phosphate, and bioactive glass, wherein the one or more particles each of hydroxyapatite β-tricalcium phosphate, α-tricalcium phosphate, and bioactive glass are sintered together to form a unitary particle; wherein the particle has a particle size of about 50 microns to about 2.5 mm, and wherein the sintered particle comprises:
   about 40 wt. % to about 60 wt. % hydroxyapatite;
   about 30 wt. % to about 50 wt. % β-tricalcium phosphate;
   about 2.5 wt. % to about 25 wt. % α-tricalcium phosphate; and
   about 5 wt. % to about 20 wt. % bioactive glass.

2. The particle of claim 1;
   wherein the particle size of the hydroxyapatite ranges from about 2 μm to about 20 μm;
   wherein the particle size of the β-tricalcium phosphate ranges from about 2 μm to about 20 μm;
   wherein the particle size of the α-tricalcium phosphate ranges from about 50 μm to about 100 μm; and
   wherein the particle size of the bioactive glass ranges from about 20 μm to about 90 μm.

3. A bone graft composition comprising a plurality of sintered particles wherein each sintered particle comprises one or more particles each of hydroxyapatite, β-tricalcium phosphate, α-tricalcium phosphate, and bioactive glass sintered together to form a unitary particle; and a carrier, wherein the unitary particle comprises:
   about 40 wt. % to about 60 wt. % hydroxyapatite;
   about 30 wt. % to about 50 wt. % β-tricalcium phosphate;
   about 2.5 wt. % to about 25 wt. % α-tricalcium phosphate; and
   about 5 wt. % to about 20 wt. % bioactive glass.

4. The bone graft composition of claim 3, further comprising additional hydroxyapatite particles having a particle size in the range of about 50 nm to about 100 μm.

5. The bone graft composition of claim 3, wherein the carrier comprises a bioresorbable polymer.

6. The bone graft composition of claim 5 wherein the carrier comprises polyethylene glycol (PEG) or methylcellulose.

7. The bone graft composition of claim 6, wherein the polyethylene glycol (PEG) comprises a PEG having a molecular weight in a range of about 500 grams/mole to about 3000 grams/mole.

8. The bone graft composition of claim 7, wherein the polyethylene glycol (PEG) comprises a PEG having a molecular weight in a range of about 1500 grams/mole to about 2500 grams/mole.

9. The bone graft composition of claim 6, wherein the composition comprises between about 30 wt % and about 50 wt % methylcellulose.

10. The bone graft composition of claim 3, wherein the carrier comprises glycerol.

11. The bone graft composition of claim 3, wherein the particles comprise about 30 wt. % to about 70 wt. % of the composition.

12. The bone graft composition of claim 3, wherein the carrier comprises about 40 wt. % to about 60 wt. % of the composition.

13. The bone graft composition of claim 4, wherein the average particle size of each sintered particle is in a range of about 50 microns to about 1 millimeter.

14. The bone graft composition of claim 13, wherein the average particle size of each sintered particle is in a range of about 250 microns to about 1 millimeter.

15. The bone graft composition of claim 3, wherein the bone graft composition exhibits a quadphasic resorption profile.

16. The bone graft composition of claim 3, wherein the unitary particle comprises a surface texturing.

17. The bone graft composition of claim 16, wherein the surface texturing is osteoconductive.

18. The bone graft composition of claim 16, wherein the surface texturing comprises nano, micro or sub-micron hydroxyapatite.

19. The bone graft composition of claim 3, further comprising demineralized bone matrix.

20. The bone graft composition of claim 19, comprising about 10% to about 90% by weight of demineralized bone matrix.

21. The bone graft composition of claim 20, comprising about 20% to about 80% by weight of demineralized bone matrix.

22. The bone graft composition of claim 21, comprising about 40% to about 60% by weight of demineralized bone matrix.

23. The bone graft composition of claim 19, comprising about 15% to about 45% by volume of demineralized bone matrix.

24. The bone graft composition of claim 19, comprising about 10% to about 50% by volume of demineralized bone matrix.

25. The bone graft composition of claim 3, wherein the carrier comprises an embedded substrate of hydroxyapatite particles,
   wherein the hydroxyapatite particles comprise micro-hydroxyapatite particles, submicron-hydroxyapatite particles, and/or nano-hydroxyapatite particles.

26. The bone graft composition of claim 25, wherein the hydroxyapatite particles of the embedded substrate have a size from about 20 nm to about 100 μm.

27. The bone graft composition of claim 26, wherein the hydroxyapatite particles of the embedded substrate have a size from about 20 nm to about 50 μm.

28. The bone graft composition of claim 27, wherein the hydroxyapatite particles of the embedded substrate have a size from about 5 μm to about 35 μm.

29. The bone graft composition of claim 28, comprising about 40 wt. % to about 55 wt. % of the embedded hydroxyapatite substrate.

30. A prefilled cartridge for a delivery device, wherein the prefilled cartridge contains the bone graft composition of any one of claims 3-29.

31. A method of preparing the particle of claim 1 comprising admixing the one or more particles of hydroxyapatite, the one or more particles of β-tricalcium phosphate, the one or more particles of α-tricalcium phosphate, and the one or more particles of bioactive glass; sintering the admixed particles at a temperature from about 500° C. to about 1700° C. to obtain sintered particles; and adjusting the size of sintered particles to be in the range of 50 microns to about 2.5 mm.

32. A method of repairing a bone defect, comprising applying the bone graft composition of any one of claims 3-29 to a subject having the bone defect and in need of repair of the bone defect.

33. The method of claim 32, wherein the subject is a mammal, or a primate mammal, or a non-human primate mammal, or a human, or wherein the mammal is a canine or dog, a feline or domestic house cat, a bovine or a cow or a bull, an ovine or a sheep or ewe, a porcine or a pig or a sow or a gilt or a boar, an equine or a horse, a cumulus or a camel, or a caprinae or a goat.

34. The method of claim 32, wherein the bone defect is a spinal bone defect.

35. A kit comprising the bone graft composition as claimed in claim 3 and a delivery device for administering the bone graft composition to a subject having a bone defect; and optionally instructions for use.

36. The kit of claim 35, further comprising an additional implantation device.

37. The kit of claim 36, wherein the additional implantation device is a 3D printed cage.

38. The kit of claim 36, wherein the additional implantation device is a loading case.

39. The bone graft composition of claim 4, wherein the additional hydroxyapatite particles are present in an amount of about 40 wt. % to about 55 wt. %.

\* \* \* \* \*